US012599444B2

(12) United States Patent
Ohashi et al.

(10) Patent No.: US 12,599,444 B2
(45) Date of Patent: Apr. 14, 2026

(54) SURGICAL IMAGE PROVIDING METHOD USING SURGICAL ROBOT, AND INFORMATION PROCESSING SYSTEM

(71) Applicant: Sysmex Corporation, Kobe (JP)

(72) Inventors: Masanao Ohashi, Kobe (JP); Yutaka Kitayama, Kobe (JP); Keiko Ishino, Kobe (JP); Arisa Ikeda, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 429 days.

(21) Appl. No.: 18/333,335

(22) Filed: Jun. 12, 2023

(65) Prior Publication Data

US 2023/0404690 A1 Dec. 21, 2023

(30) Foreign Application Priority Data

Jun. 17, 2022 (JP) ................................. 2022-097809

(51) Int. Cl.
A61B 34/30 (2016.01)
A61B 17/29 (2006.01)
(Continued)

(52) U.S. Cl.
CPC .............. A61B 34/30 (2016.02); A61B 17/29 (2013.01); A61B 34/10 (2016.02); A61B 34/20 (2016.02);
(Continued)

(58) Field of Classification Search
None
See application file for complete search history.

(56) References Cited

U.S. PATENT DOCUMENTS 8,418,073 B2 * 4/2013 Mohr ................. A61B 18/1233
715/764
2008/0058612 A1 * 3/2008 Ohyu ..................... G16H 20/10
600/300
(Continued)

FOREIGN PATENT DOCUMENTS

EP 4509084 A1 * 2/2025 .............. B25J 13/06
GB 2593913 A * 10/2021 ............. A61B 34/74
(Continued)

OTHER PUBLICATIONS

The extended European search report issued on Oct. 30, 2023 in a counterpart European patent application No. 23179182.3.

*Primary Examiner* — Ted W Barnes
(74) *Attorney, Agent, or Firm* — Crowell & Moring LLP

(57) ABSTRACT

Disclosed is a surgical image providing method using a surgical robot for providing an image of a surgery performed by the surgical robot, the surgical robot including an arm device to which a surgical instrument is attached, and an operation device that an operator operates to drive the arm device. The method includes: obtaining a state log indicating a state of an operation target of the operation device, the state being changed according to an operation of the operator to the operation target; generating a reconstructed image visualizing the operation of the operator to the operation target, on the basis of the state log; and providing a surgical image in which a motion image showing a motion of the surgical robot or the surgical instrument is associated with the reconstructed image.

13 Claims, 33 Drawing Sheets

(51) Int. Cl.

| | | |
|---|---|---|
| *A61B 34/10* | (2016.01) | |
| *A61B 34/20* | (2016.01) | |
| *A61B 90/00* | (2016.01) | |

(52) U.S. Cl.
CPC ...... *A61B 90/361* (2016.02); *A61B 2034/105* (2016.02); *A61B 2034/2055* (2016.02); *A61B 2034/301* (2016.02); *A61B 2034/305* (2016.02)

(56) References Cited

U.S. PATENT DOCUMENTS

| | | | | |
|---|---|---|---|---|
| 2010/0228249 A1 * | 9/2010 | Mohr | .............. | A61B 1/000096 |
| | | | | 715/764 |
| 2012/0221147 A1 * | 8/2012 | Goldberg | .............. | G16H 20/40 |
| | | | | 700/264 |
| 2013/0211418 A1 * | 8/2013 | Lim | .......................... | B06B 1/18 |
| | | | | 340/407.2 |
| 2014/0195052 A1 * | 7/2014 | Tsusaka | ................. | A61B 34/30 |
| | | | | 700/260 |
| 2020/0107891 A1 * | 4/2020 | Ohashi | ................... | B25J 9/1697 |
| 2021/0315647 A1 * | 10/2021 | Tojo | ........................ | A61B 34/25 |
| 2021/0401527 A1 * | 12/2021 | Hassan | ................... | A61B 34/30 |
| 2023/0145790 A1 * | 5/2023 | Walker | ................... | A61B 34/30 |
| | | | | 606/1 |
| 2024/0050175 A1 * | 2/2024 | Kishida | ................. | A61B 34/35 |

FOREIGN PATENT DOCUMENTS

| | | | | | |
|---|---|---|---|---|---|
| JP | 2022500163 A | * | 1/2022 | ............. | G16H 40/40 |
| WO | WO-2019117926 A1 | * | 6/2019 | ............. | A61B 90/37 |
| WO | WO-2021247050 A1 | * | 12/2021 | ......... | A61B 1/00009 |

* cited by examiner 4 (SURGICAL ROBOT)

TO ARM DEVICE 1, OPERATION DEVICE 2, STORAGE DEVICE 310

<u>5</u>

TO CONTROL DEVICE 3

FIG. 13

| UNIT | PARTS | CURRENT VALUE |
|------|-------|---------------|
| | | STATE LOG |
| HAND CONTROLLER (RIGHT) | 1_1 LINK | -15.966 |
| HAND CONTROLLER (RIGHT) | 1_2 LINK | 8.369 |
| HAND CONTROLLER (RIGHT) | 1_3 LINK | -14.874 |
| HAND CONTROLLER (RIGHT) | 1_4 LINK | 107.449 |
| HAND CONTROLLER (RIGHT) | 1_5 LINK | 21.104 |
| HAND CONTROLLER (RIGHT) | 1_6 LINK | 7.046 |
| HAND CONTROLLER (RIGHT) | 1_7 LINK | -100.145 |
| HAND CONTROLLER (RIGHT) | 1_GRIP ANGLE | 0.000 |
| HAND CONTROLLER (LEFT) | 1_1 LINK | 20.001 |
| HAND CONTROLLER (LEFT) | 1_2 LINK | 2.011 |
| HAND CONTROLLER (LEFT) | 1_3 LINK | -7.422 |
| HAND CONTROLLER (LEFT) | 1_4 LINK | 94.770 |
| HAND CONTROLLER (LEFT) | 1_5 LINK | -19.916 |
| HAND CONTROLLER (LEFT) | 1_6 LINK | 165.900 |
| HAND CONTROLLER (LEFT) | 1_7 LINK | 68.606 |
| HAND CONTROLLER (LEFT) | 1_GRIP ANGLE | 2.024 |

FIG. 14

| UNIT | PARTS | CURRENT TIME (H:M:S) | CURRENT VALUE |
|---|---|---|---|
| HAND CONTROLLER (LEFT) | 1_GRIP ANGLE | 00:00:00 | 0.000 |
| | | 00:00:01 | 0.015 |
| | | 00:00:02 | 0.505 |
| | | 00:00:03 | 1.302 |
| | | 00:00:04 | 2.024 |
| | | 00:00:05 | 3.455 |
| | | ... | ... |

FIG. 15

OPERATION LOG

| UNIT | PARTS | CURRENT VALUE |
|---|---|---|
| OPERATION ARM 1 | 1_1 LINK | -0.001 |
| OPERATION ARM 1 | 1_2 LINK | 46.343 |
| OPERATION ARM 1 | 1_3 LINK | -3.688 |
| OPERATION ARM 1 | 1_4 LINK | -126.481 |
| OPERATION ARM 1 | 1_5 LINK | 197.814 |
| OPERATION ARM 1 | 1_6 LINK | 4.414 |
| OPERATION ARM 1 | 1_7 LINK | -126.026 |
| OPERATION ARM 1 | 1_8 LINK | -37.454 |
| OPERATION ARM 1 | 1_9 LINK | 6.501 |
| OPERATION ARM 1 | 1_10 LINK | -19.866 |
| OPERATION ARM 1 | 1_11 LINK | 3.243 |
| OPERATION ARM 1 | 1_12 LINK | 46.090 |
| OPERATION ARM 2 | 2_1 LINK | -0.002 |
| OPERATION ARM 2 | 2_2 LINK | 47.590 |
| OPERATION ARM 2 | 2_3 LINK | -1.846 |
| OPERATION ARM 2 | 2_4 LINK | -123.051 |

FIG. 16

| UNIT | PARTS | CURRENT TIME (H:M:S) | CURRENT VALUE |
|---|---|---|---|
| OPERATION ARM 1 | 1_1 LINK | 00:00:00 | 0.000 |
| | | 00:00:01 | 0.000 |
| | | 00:00:02 | 5.456 |
| | | 00:00:03 | 10.866 |
| | | 00:00:04 | 30.122 |
| | | 00:00:05 | 35.934 |
| | | ... | ... |

430

FIG. 22
LEFT FOOT AND RIGHT FOOT IN NON-HOVER STATE
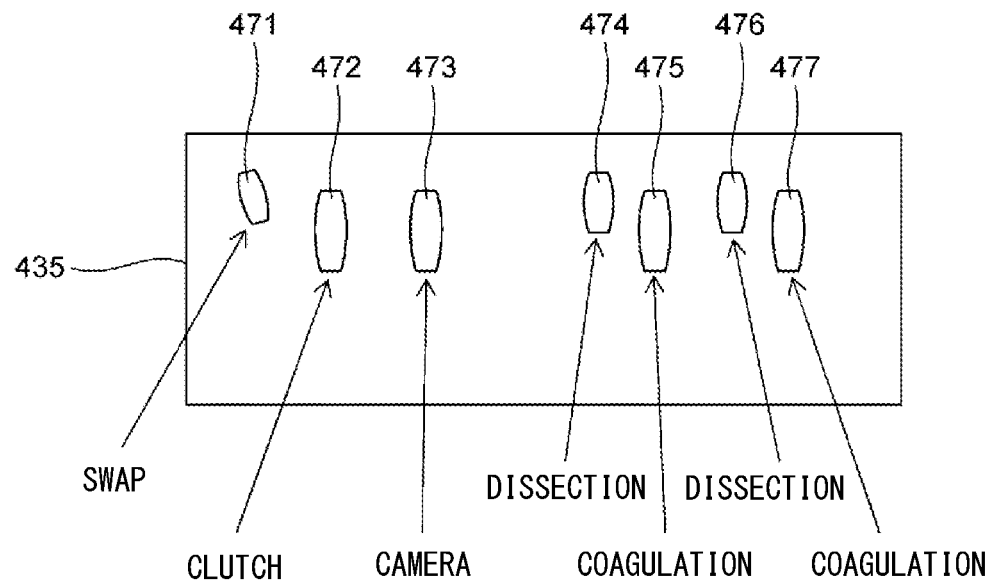
LEFT FOOT AND RIGHT FOOT IN OPERATION PREPARING STATE
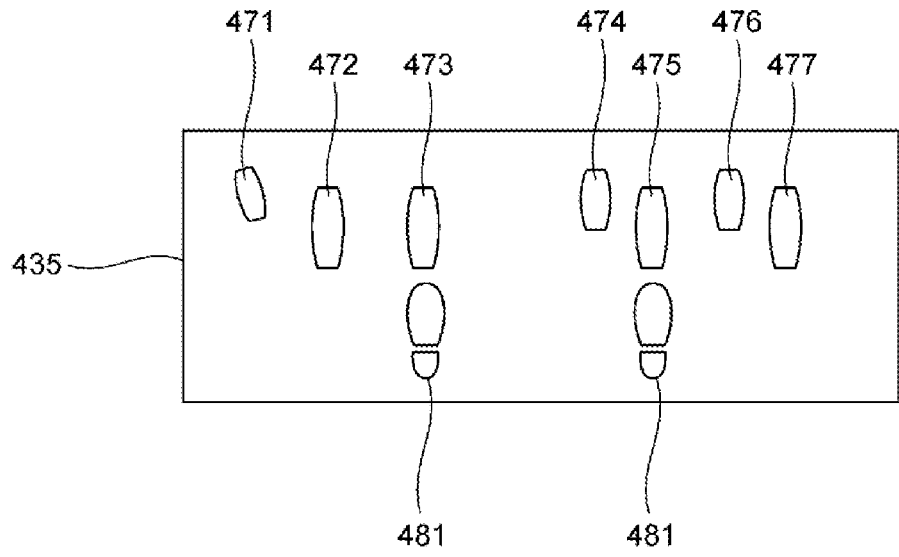

FIG. 23
RIGHT FOOT STEPPING ON FOOT PEDAL
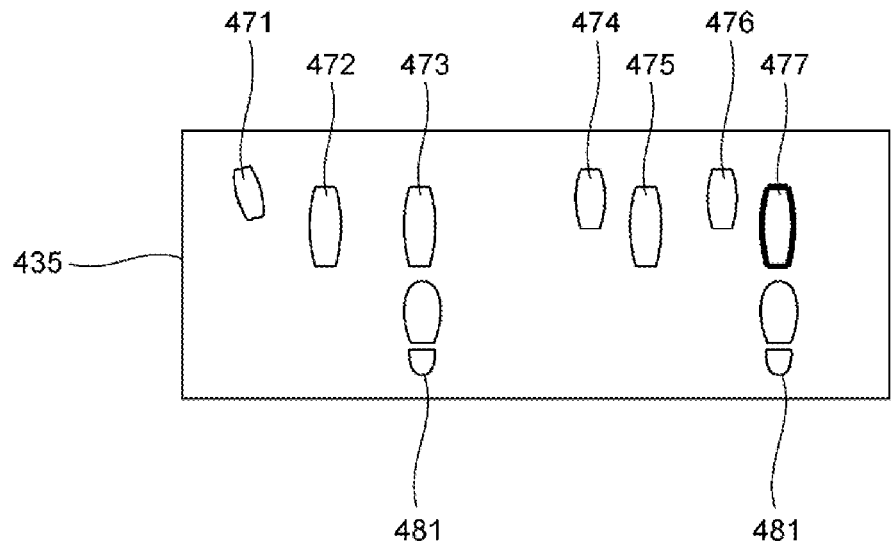
LEFT FOOT STEPPING ON FOOT PEDAL
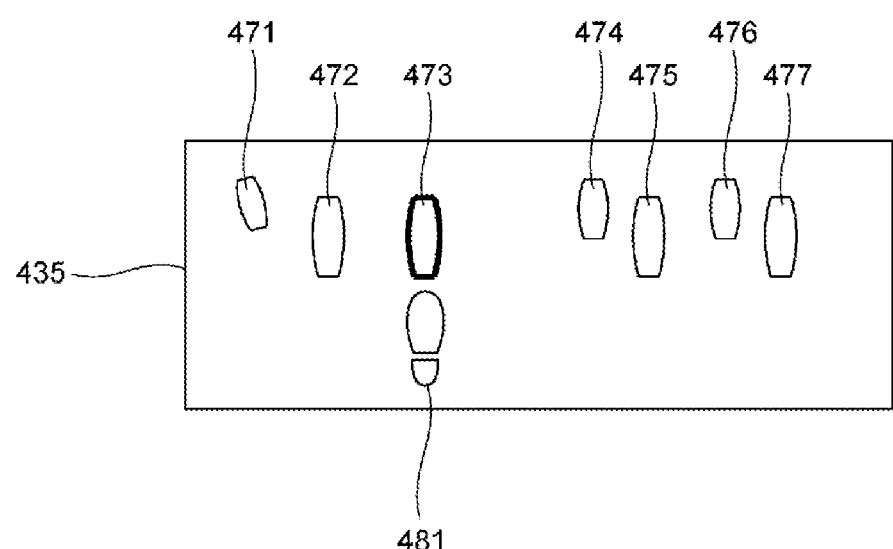

INFORMATION PROCESSING DEVICE

INFORMATION PROCESSING DEVICE

START

S2

GENERATE FIRST TO THIRD RECONSTRUCTED
IMAGES, AND SCHEMATIC IMAGE

S3

GENERATE SURGICAL IMAGE

S4

ADD ADDITIONAL INFORMATION

S5

PROVIDE SURGICAL IMAGE

END

INFORMATION PROCESSING DEVICE

S4: ADD ADDITIONAL INFORMATION

S11

ADD INFORMATION INDICATING ALREADY VIEWED PART AND
NUMBER OF VIEWS

S12

ADD INFORMATION INDICATING PRESENCE/ABSENCE OF ATTACHED
SURGICAL INSTRUMENT, AND KIND OF SURGICAL INSTRUMENT

RETURN

INFORMATION PROCESSING DEVICE

SURGICAL IMAGE PROVIDING METHOD USING SURGICAL ROBOT, AND INFORMATION PROCESSING SYSTEM

RELATED APPLICATIONS

This application claims priority to Japanese Patent Application No. 2022-097809, filed on Jun. 17, 2022, the entire content of which is incorporated herein by reference.

BACKGROUND OF THE INVENTION

1. Field of the Invention

The present invention relates to a surgical image providing method using a surgical robot, and an information processing system.

2. Description of the Related Art

Conventionally, surgeries using surgical robots have been performed. A surgical robot is provided with a console (operation device) and a surgical robot arm (arm device). The surgical robot arm is equipped with surgical instruments. Surgical instruments are attached to the surgical robot arm, and the surgical robot arm and the surgical instruments are operated by an operator operating the console. Every operator is desirably able to improve the level of his/her skill of operating the console, so that patients can undergo surgeries with security.

International Publication WO2021/247050 discloses a system in which a surgery performed with a surgical robot in an operation room is captured by a depth camera and stored, and an image obtained by schematizing the captured image can be reproduced after the surgery. In addition, in the system disclosed in International Publication WO2021/247050, histories of the state of the surgical robot arm, the state of a handheld UID of the console, and the like are stored as system data. The stored system data are used for schematizing the captured image while reconstructing the positions, orientations, and movements of the robot arm and the surgical instruments.

SUMMARY OF THE INVENTION

In the system disclosed in International Publication WO2021/247050, however, only the image obtained by schematizing the captured image showing the state of the surgery by the surgical robot can be confirmed, and it is difficult to confirm how the operator was operating the console during the surgery.

In view of the above problem, an object of the present invention is to provide a surgical image providing method using a surgical instrument, and an information processing system which enable easy and accurate confirmation of the motion of a surgical robot or surgical instruments, and an operation to an operation target for realizing the motion.

The present invention is a method for providing a surgical image (400), using a surgical robot (4) for providing an image (400) of a surgery performed by the surgical robot (4), and the surgical robot (4) includes an arm device (1) to which a surgical instrument (121 to 124) is attached, and an operation device (2) that an operator operates to drive the arm device (1). The method includes: obtaining a state log indicating a state of an operation target (221, 231 to 237, 211) of the operation device (2), the state being changed according to an operation of the operator to the operation target (221, 231 to 237, 211) (S1); generating a reconstructed image (432a, 432b, 434, 435, 440) visualizing the operation of the operator to the operation target (221, 231 to 237, 211), on the basis of the state log (S2); and providing a surgical image (400) in which a motion image (401 to 404) showing a motion of the surgical robot (4) or the surgical instrument (121 to 124) is associated with the reconstructed image (432a, 432b, 434, 435, 440) (S5).

An information processing system (5) according to the present invention includes: a storage device (310) configured to store a state log therein, the state log indicating a state of an operation target (221, 231 to 237, 211) of an operation device (2) that is controlled by an operator to drive an arm device (1) of a surgical robot (4) to which a surgical instrument (121 to 124) is attached, the state of the operation target being changed according to an operation of the operator to the operation target; and an information processing device (320) configured to generate a reconstructed image (432a, 432b, 434, 435, 440) visualizing an operation of the operator to the operation target (221, 231 to 237, 211) on the basis of the state log stored in the storage device (310), and provide a surgical image (400) in which a motion image (401 to 404) showing a motion of the surgical robot (4) or the surgical instrument (121 to 124) is associated with the reconstructed image (432a, 432b, 434, 435, 440).

BRIEF DESCRIPTION OF THE DRAWINGS

FIG. 13 illustratively shows current values constituting a state log transmitted from the operation device to the control device, according to the embodiment;

FIG. 14 shows an example of the state log according to the embodiment;

FIG. 15 illustratively shows current values constituting an operation log transmitted from the arm device to the control device, according to the embodiment;

FIG. 16 shows an example of the operation log according to the embodiment;

FIG. 22 schematically shows a configuration and transition of an image regarding the state of foot pedals, according to the embodiment;

FIG. 23 schematically shows a configuration and transition of an image regarding the state of the foot pedals, according to the embodiment;

DETAILED DESCRIPTION OF THE PREFERRED EMBODIMENTS

Figure 1:
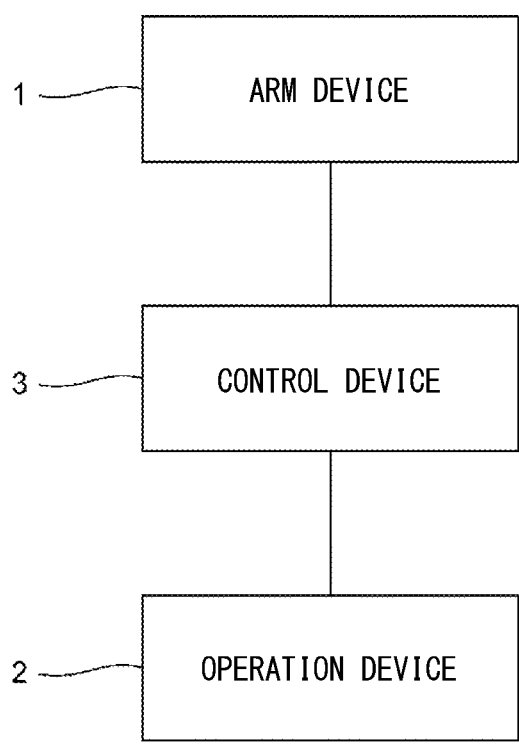
FIG. 1 is a block diagram showing a configuration of a surgical robot according to an embodiment.

FIG. 1 is a block diagram showing a configuration of a surgical robot 4.

The surgical robot 4 is a device used for an endoscopic operation. The surgical robot 4 includes an arm device 1, an operation device 2, and a control device 3 that controls the arm device 1 and the operation device 2. The control device 3 is built in the arm device 1. The operation device 2 and the arm device 1 with the built-in control device 3 may be installed in the same facility, or may be installed in different facilities via a network.

Figure 2:
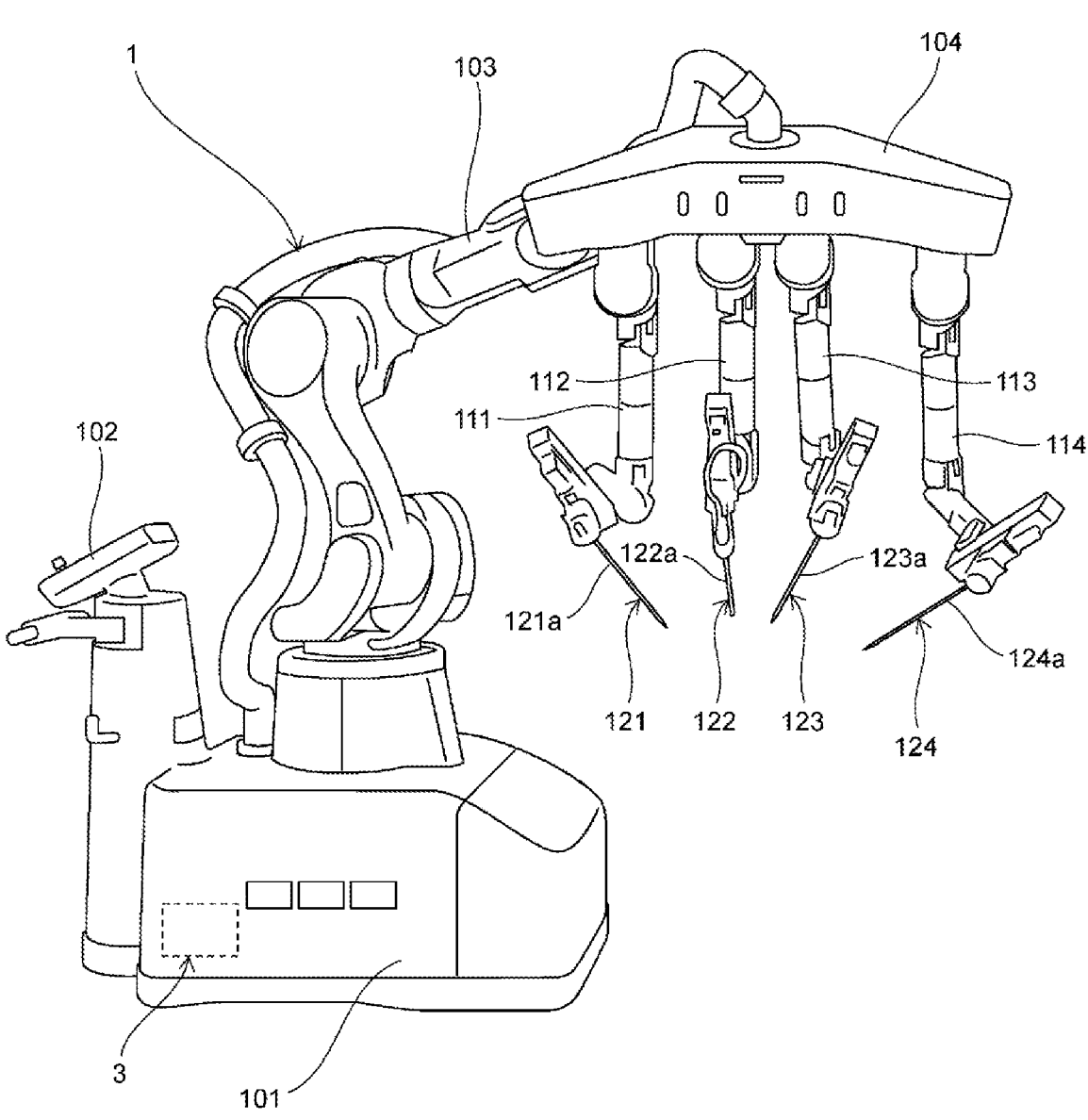
FIG. 2 is a perspective view showing the appearance of an arm device according to the embodiment.

FIG. 2 is a perspective view showing the appearance of the arm device 1.

The arm device 1 is a patient-side device including a plurality of arms to which endoscopes and forceps are attachable. The arm device 1 is operated according to a drive instruction that is transmitted from the control device 3 when the operation device 2 is operated by an operator who is a doctor.

The arm device 1 includes a base 101, an operation unit 102, a base arm 103, a support member 104, and arms 111 to 114. Surgical instruments 121 to 124 are detachably attached to the arms 111 to 114, respectively.

The operation unit 102 is disposed on the base 101, and includes a display part and an input part. The operator operates the input part of the operation unit 102 while viewing the display part of the operation unit 102 to set a moving speed and the like of the arms 111 to 114 of the arm device 1. The base arm 103 is an arm having a proximal end disposed on the base 101, and a plurality of joints. The support member 104 has an upper surface pivotably connected to a distal end of the base arm 103. The support member 104 moves according to movement of the distal end of the base arm 103, and pivots around an axis of the distal end of the base arm 103.

The arms 111 to 114 have upper ends disposed on a lower surface of the support member 104. Each of the arms 111 to 114 has twelve links and joints between the links. The arms 111 to 114 have, at lower ends thereof, holder members configured to enable attachment/detachment of surgical instruments, and the surgical instruments 121 to 124 are attached to the respective holder members.

The surgical instruments 121 to 124 have elongated rod parts 121a to 124a. In the endoscopic operation, the rod parts 121a to 124a of the surgical instruments 121 to 124 are inserted into the body of a patient through trocars inserted in the abdomen of the patient. In this embodiment, the surgical instruments 121, 123, 124 are forceps, and the surgical instruments (forceps) 121, 124 are so-called grasping forceps. The surgical instrument (forceps) 123 is a so-called electrocautery, and has, at a tip, a hand capable of dissection and coagulation. The surgical instrument 122 is an endoscope. The surgical instrument (endoscope) 122 is a 3D video scope, for example. Hereinafter, the surgical instrument 122 is also referred to as "endoscope 122".

The forceps are not limited to grasping forceps, and may be other kinds of forceps such as hemostatic forceps and dissection/ligature forceps, or electrical instruments such as electrocauteries. In the middle of the endoscopic operation, the surgical instruments 121 to 124 may be replaced with other kinds of surgical instruments according to need.

Figure 3:
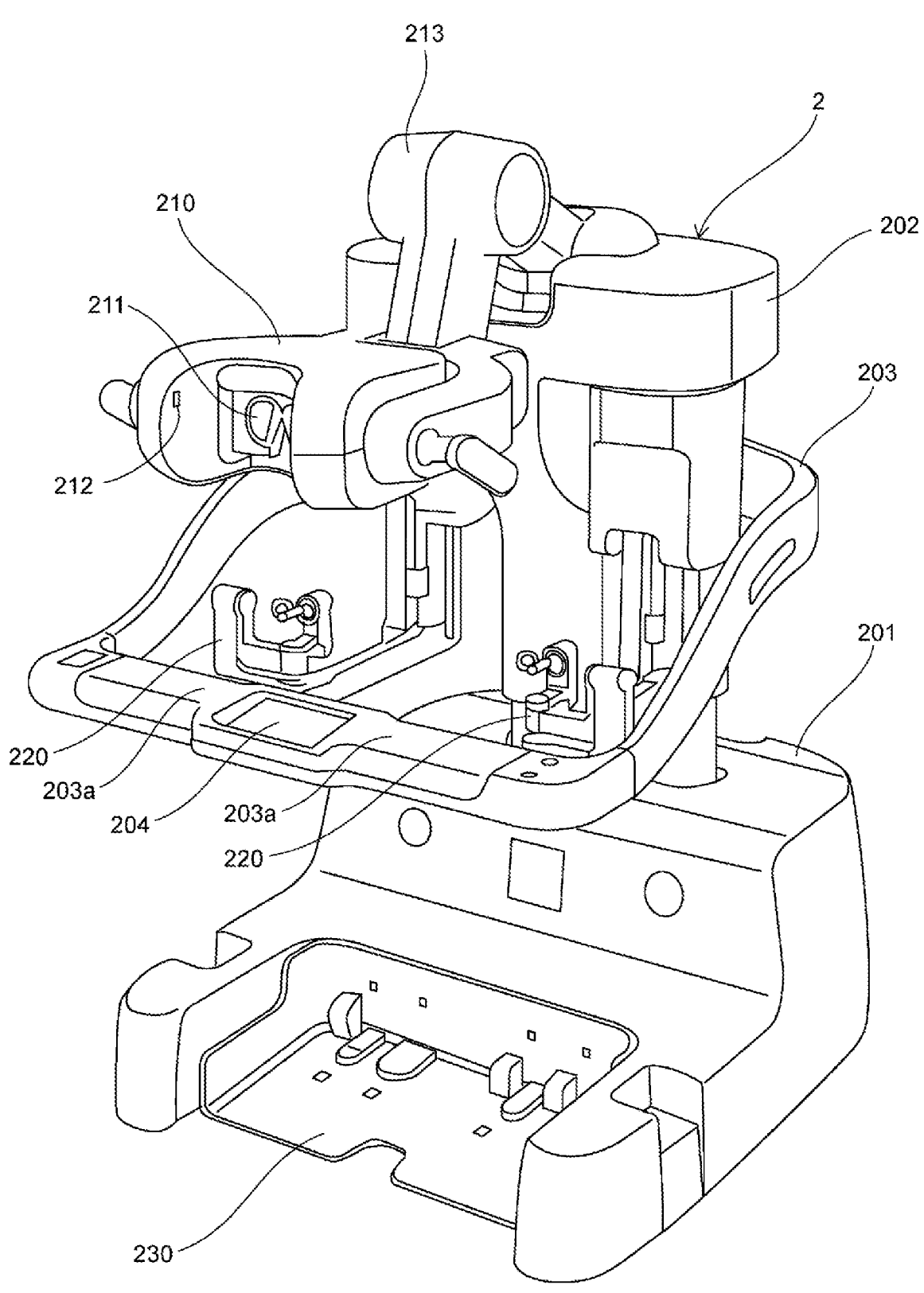
FIG. 3 is a perspective view showing the appearance of an operation device according to the embodiment.

FIG. 3 is a perspective view showing the appearance of the operation device 2.

The operation device 2 is an operator-side device that is operated in the endoscopic operation by the operator who is a doctor to drive the arm device 1.

The operation device 2 includes a base 201, a support member 202, a frame member 203, an operation panel 204, a viewer unit 210, two hand controllers 220, and a foot unit 230.

The support member 202 is disposed on an upper part of the base 201 so as to be movable up and down. The frame member 203 is disposed on the support member 202. The operation panel 204 is disposed on an upper surface of a front center part of the frame member 203. Arm rests 203a are formed to the left and right of the operation panel 204 on which the operator can put his/her elbows when operating the hand controller 220. The height of the arm rests 203a can be changed by moving the support member 202 up and down with respect to the base 201.

The viewer unit 210 is supported by a distal end of an arm 213 disposed on an upper surface of the support member 202. The height of the viewer unit 210 can be changed by pivoting a joint of the arm 213. The viewer unit 210 includes a display part (hereinafter referred to as "viewer") 211, and head sensors 212. The viewer 211 displays a video (endoscopic image) captured by the endoscope 122. The head sensors 212 are disposed so as to sandwich an area in front of the viewer 211, and are transmission-type photoelectric sensors. When the operator is looking into the viewer 211, the head of the operator is close to the viewer 211 and blocks light between the head sensors 212, whereby the operator's viewing the viewer 211 is detected.

Each of the two hand controllers 220 includes seven links and joints between the links, and are disposed on the support member 202. The left and right hand controllers 220 are input devices for the operator to operate the arms 111 to 114 of the arm device 1 with the left hand and the right hand, respectively. The configuration of the hand controllers 220 will be described with reference to FIG. 4 later.

The foot unit 230 is disposed on the front side of a lower part of the base 201 so as to be movable forward and backward. The foot unit 230 is an input device for the operator to operate the arm device 1 with the left foot and the right foot. The configuration of the foot unit 230 will be described with reference to FIG. 5 later. By operating the operation panel 204, the operator can change settings of the operation device 2, such as the height of the arm rests 203a, the height of the viewer unit 210, the position of the foot unit 230 in the front-rear direction, and the like.

Figure 4:
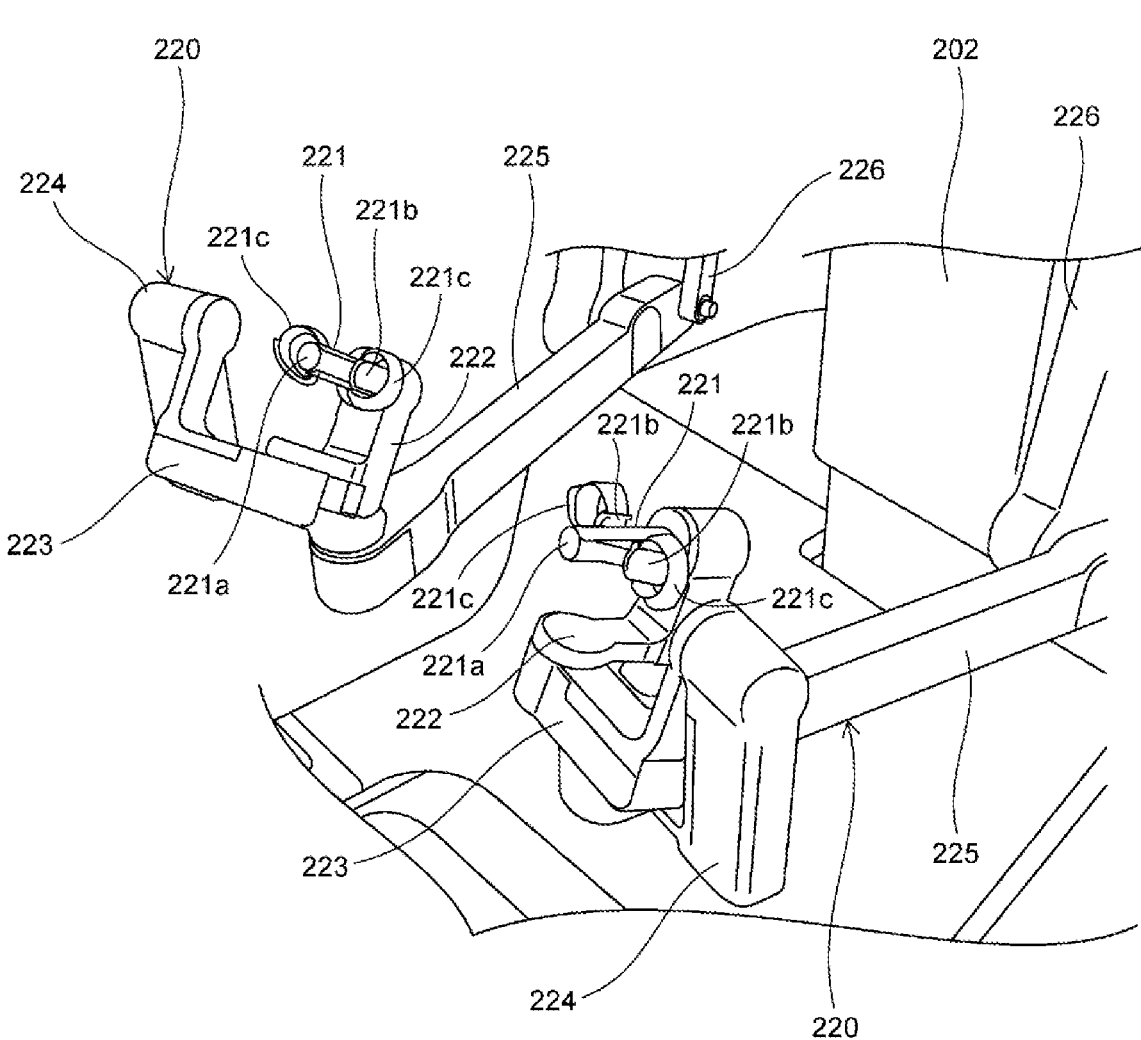
FIG. 4 is a perspective view showing the appearance of a hand controller according to the embodiment.

FIG. 4 is a perspective view showing the appearance of the hand controller 220.

The two hand controllers 220 are configured to be symmetrical in the left-right direction. Each hand controller 220 includes an operation part 221 and six movable parts 222 to 226.

The operation part 221 includes a spindle 221a, a pair of movable plates 221b, and a pair of hook-and-loop fasteners 221c. The operation part 221 is a part that the operator directly operates with his/her hand and fingers, and is an operation target that the operator touches and operates.

The spindle 221a is a cylindrical member disposed on the movable part 222. The pair of movable plates 221b are plate-shaped members sandwiching the spindle 221a. Each movable plate 221b is disposed on the corresponding spindle 221a such that an end part thereof closer to the movable part 222 approaches and separates from the spindle 221a. The hook-and-loop fasteners 221c are disposed on the movable plates 221b. The operation part 221 includes an encoder 261 (see FIG. 12) for detecting opening/closing angles of the pair of movable plates 221b, and an encoder 271 (see FIG. 12) for detecting an amount of rotation of the operation part 221 with respect to the movable part 222.

The movable parts 222 to 226 constitute an arm connecting the operation part 221 and the support member 202. The movable parts 222 to 226 are parts that the operator does not touch, i.e., parts that the operator indirectly operates through the operation part 221. Each of joints of the arm constituted by the movable parts 222 to 226 is formed by two adjacent movable parts rotating around a shaft. The movable parts 222 to 226 are respectively provided with encoders 272 to 276 (see FIG. 12) each for detecting an amount of rotation of an adjacent movable part on the side opposite to the operation part 221. That is, the encoders 271 to 276 are disposed one by one at the ends of the seven links of the hand controller 220.

The encoder may not necessarily be used for detecting the amount of rotation of each movable part. Various types of state detectors, such as an encoder and a sensor for detecting the conditions of the detection target such as the position, rotation amount, angle, and presence/absence, may be used.

Before starting a surgery, the operator presses his/her thumb and forefinger against the pair of movable plates 221b so as to pinch the movable plates 221b. In this state, the hook-and-loop fastener 221c is fastened to the thumb and forefinger pinching the pair of movable plates 221b. Thus, the thumb and forefinger of the left hand are fixed to the operation part 221 of the left hand controller 220, and the thumb and forefinger of the right hand are fixed to the operation part 221 of the right hand controller 220. The fingers for pinching the pair of movable plates 221b are not limited to the thumb and forefinger, and may be selected by the operator considering ease of operation. For example, the fingers for pinching the pair of movable plates 221b may be the thumb and middle finger.

When the operator has performed an operation of moving the operation part 221 during the surgery, the joints of the hand controller 220 rotate around the shafts according to the movement of the operation part 221. Then, on the basis of the output values of the encoders 271 to 276, a target arm in the arm device 1 is driven, and the surgical instrument attached to this arm moves. In the case where forceps are attached to the target arm, if the operator performs an operation of opening and closing the pair of movable plates 221b of the operation part 221 during the surgery, the tip of the forceps attached to the arm is opened and closed on the basis of the output value of the encoder 261 of the operation part 221.

Figure 5:
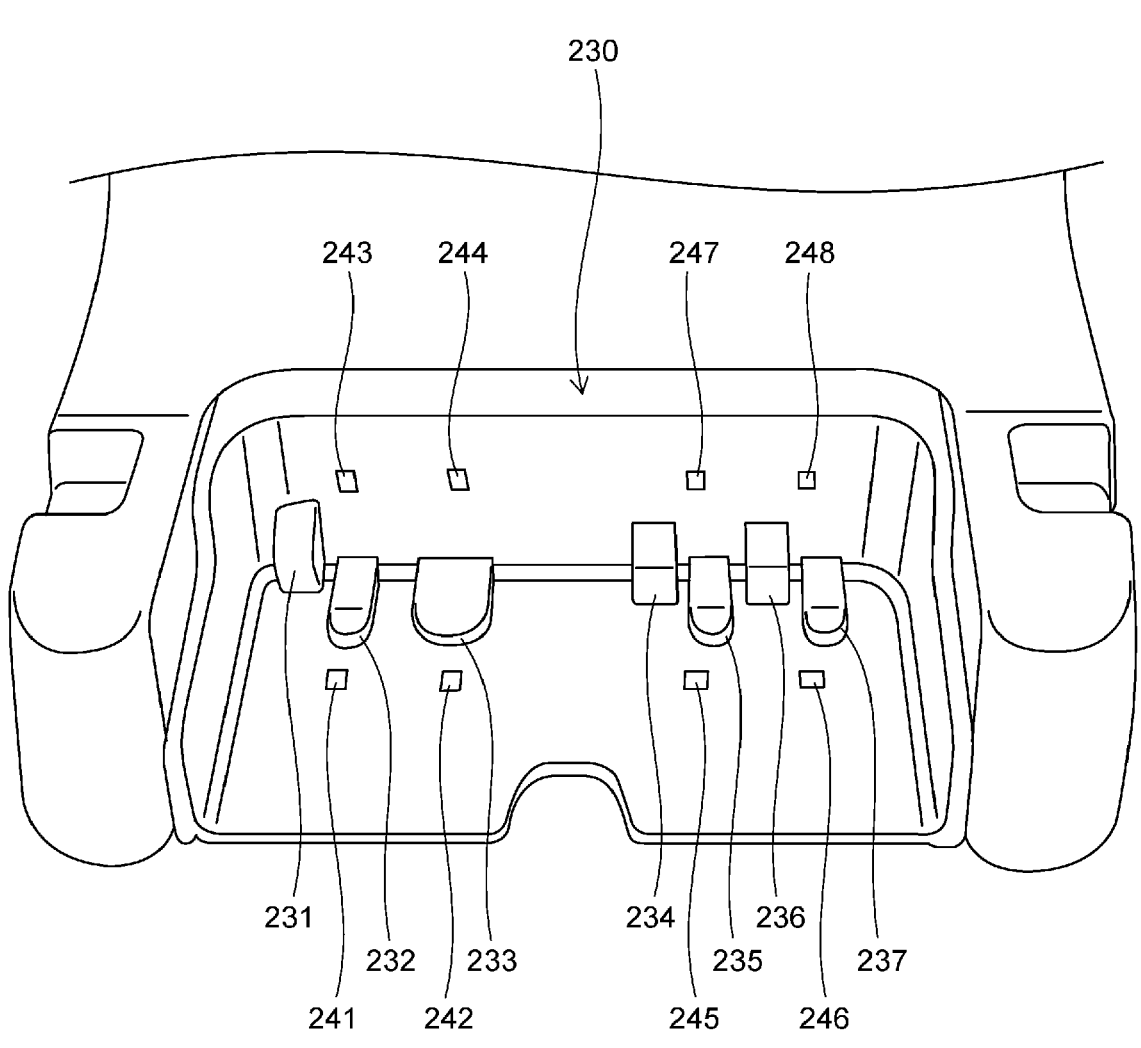
FIG. 5 is a perspective view showing the appearance of a foot unit according to the embodiment.

FIG. 5 is a perspective view showing the appearance of the foot unit 230.

The foot unit 230 includes foot pedals 231 to 237, and foot sensors 241 to 248.

The operator steps on the foot pedals 231 to 237 to perform an input for operating the arm device 1. That is, the foot pedals 231 to 237 are manipulators for performing a predetermined input. If an electrocautery is attached to the target arm, the foot pedals 234 to 237 are manipulators for switching the electrocautery between an energized state and an non-energized state.

When the foot pedal 231 is stepped on, the surgical instrument to be operated by the right hand controller 220 is switched to either of the surgical instruments 123, 124. The foot pedal 232 is a clutch pedal. While the foot pedal 232 is being stepped on, operation of the hand controller 220 is not transferred to the arm device 1. The foot pedal 233 is a camera pedal. While the foot pedal 233 is being stepped on, the arm having the endoscopes 122 attached thereto can be operated by the hand controllers 220.

The foot pedals 234, 236 are dissection pedals. While the foot pedals 234, 236 are being stepped on, a radio frequency is applied to the tip of the forceps (electrocautery) so as to enable dissection by the forceps (electrocautery). The foot pedals 235, 237 are coagulation pedals. While the foot pedals 235, 237 are being stepped on, a radio frequency is applied to the tip of the forceps (electrocautery) so as to enable coagulation by the forceps (electrocautery).

The foot pedals 231 to 237 are respectively provided with limit sensors 281 to 287 (see FIG. 12) for detecting whether or not the corresponding foot pedals are stepped on. Thus, whether or not the foot pedals 231 to 237 are stepped on is detected.

The foot sensors 241 to 248 are reflection-type photoelectric sensors for detecting the positions of the feet of the operator. The foot sensors 241 to 244 detect whether or not the left foot is positioned on the foot pedals 231 to 233, and the foot sensors 245 to 248 detect whether or not the right foot is positioned on the foot pedals 234 to 237. Specifically, the foot sensors 241 to 248 detect: a hover state including a state where the feet are in front of the foot pedals, a state where the feet are above the foot pedals, and a state where the foot pedals are stepped on; and a non-hover state where the feet are not present in the foot unit 230.

Figure 6:
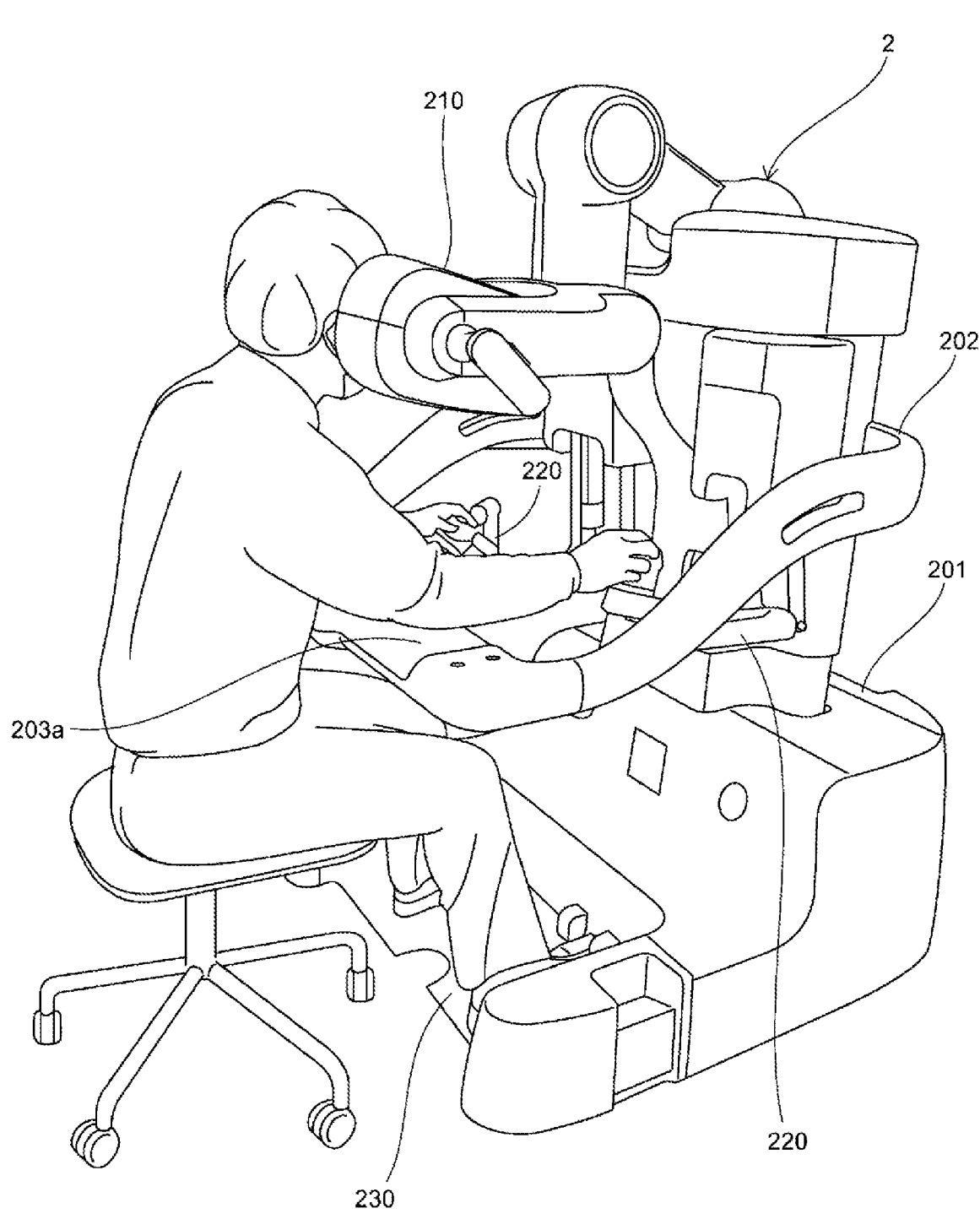
FIG. 6 is a perspective view showing the state where an operator uses the operation device, according to the embodiment.

FIG. 6 is a perspective view showing the state where the operator uses the operation device 2.

Before starting the surgery, a patient lying on a surgical table is positioned beneath the surgical instruments 121 to 124, trocars are inserted into the abdomen of the patient, and the surgical instruments 121 to 124 are inserted into the body of the patient through the trocars. The operator, sitting on a chair, puts his/her arms on the arm rests 203a, and puts his/her feet inside or in front of the foot unit 230. Using the hook-and-loop fastener 221c (see FIG. 4), the operator fastens the thumb and forefinger of each of his/her hands to the movable plate 221b. Then, the operator inserts his/her head into the viewer unit 210, and looks into the viewer 211. When the head sensor 212 detects that the head of the operator is positioned in the viewer unit 210, the operator is allowed to operate the arm device 1 through the operation device 2.

When the surgery has started, the operator operates the left and right operation parts 221 (see FIG. 4) to input a grasping operation that causes the forceps to perform a grasping motion, or input a moving operation that causes the tip of the forceps to move. According to the operation inputted to the operation device 2 by the operator, the arms 111 to 114 and the surgical instruments 121 to 124 of the arm device 1 are driven. Thus, various surgical operations are performed.

The operator moves his/her head away from the viewer unit 210 when he/she makes an instruction to an assistant present in the operating room, when he/she takes a break, and when he/she has finished the surgery, for example. When the head sensor 212 detects that the head of the operator is not positioned in the viewer unit 210, the operator cannot operate the arm device 1 through the operation device 2. This prevents the arm device 1 from being erroneously operated.

Figure 7:
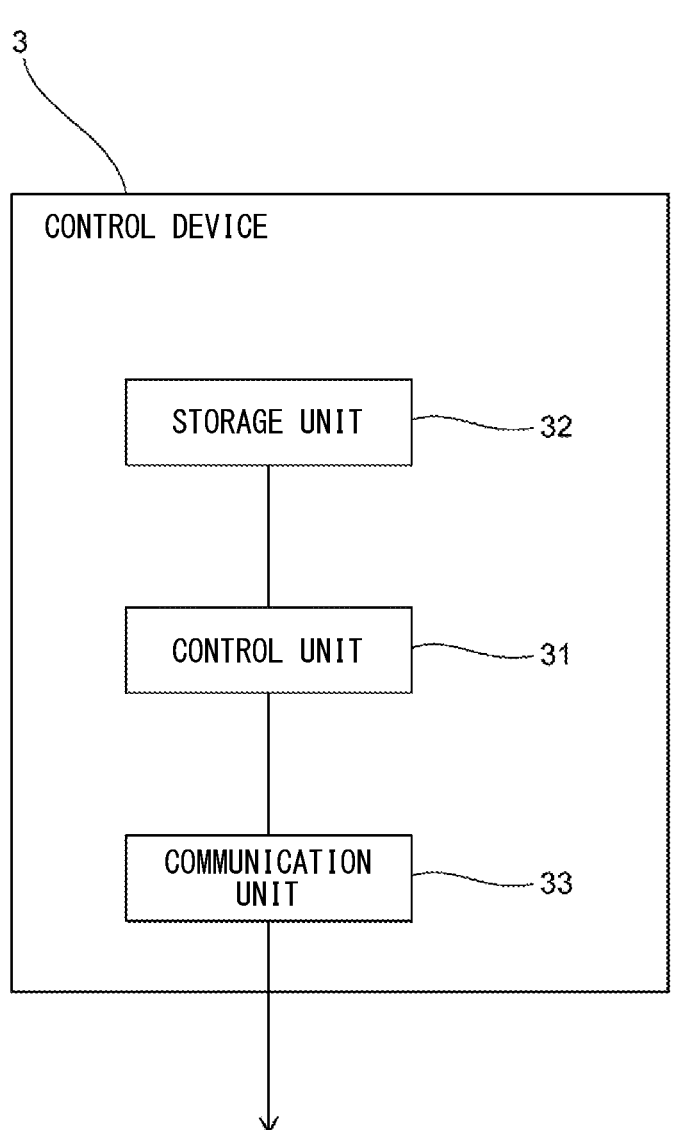
FIG. 7 is a block diagram showing a configuration of a control device according to the embodiment.

FIG. 7 is a block diagram showing the configuration of the control device 3.

The control device 3 includes a control unit 31, a storage unit 32, and a communication unit 33. The control unit 31 is implemented by a CPU, for example. The control unit 31 executes a computer program stored in the storage unit 32, thereby controlling the hardware components of the control device 3, and executing various processing. The storage unit 32 is implemented by an SSD, an HDD, or the like, for example. The communication unit 33 includes a communication interface that is communicable with the arm device 1, the operation device 2, and a storage device 310 (see FIG. 8) on the basis of a predetermined communication standard.

Figure 8:
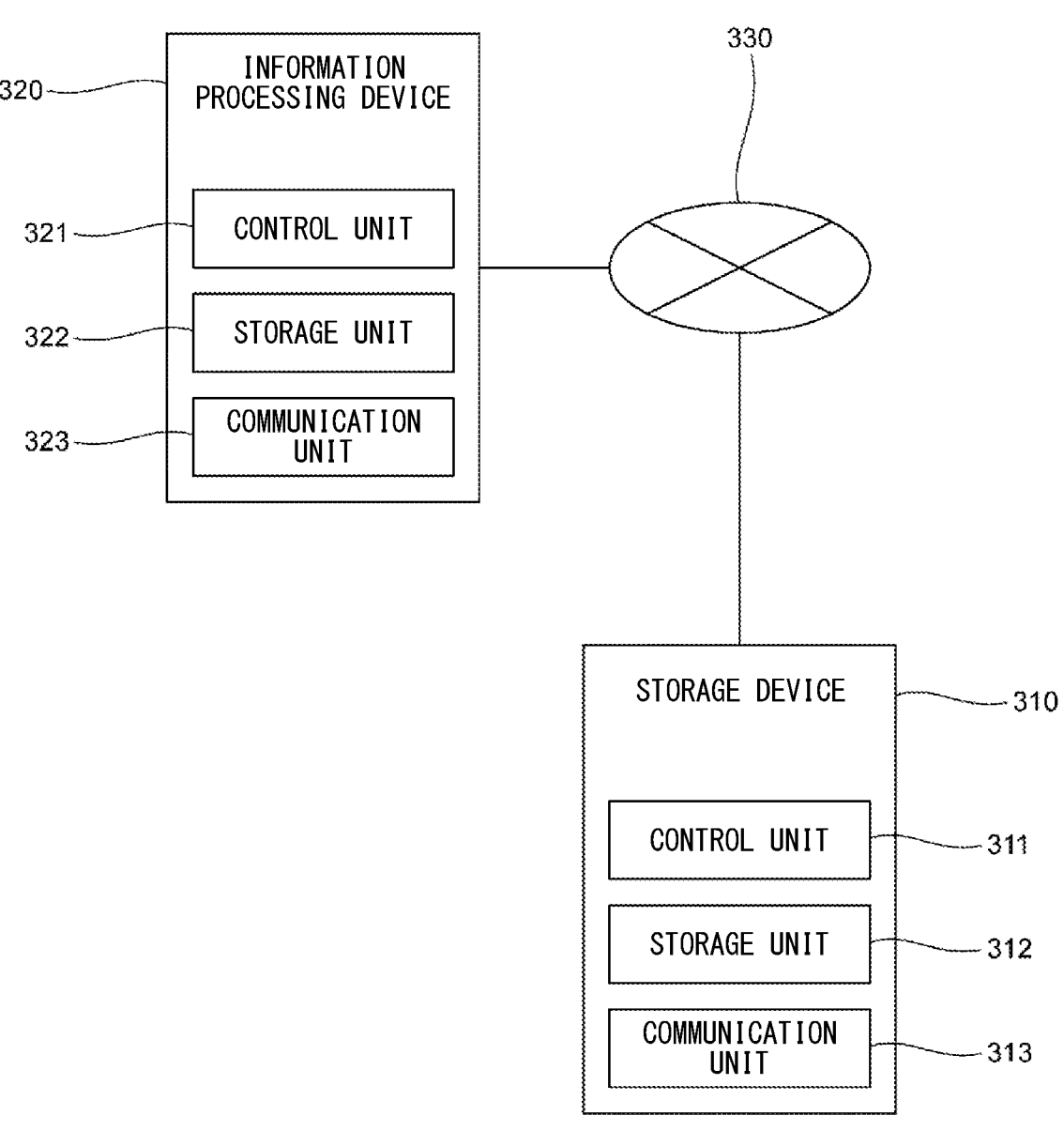
FIG. 8 is a block diagram showing a configuration of an information processing system according to the embodiment.

FIG. 8 is a block diagram showing the configuration of an information processing system 5.

The information processing system 5 includes a storage device 310 and an information processing device 320. A network 330 is the Internet, for example.

The storage device 310 includes a control unit 311, a storage unit 312, and a communication unit 313. The control unit 311 is implemented by a CPU, for example. The control unit 311 executes a computer program stored in the storage unit 312, thereby controlling the hardware components of the storage device 310, and executing various processing. The storage unit 312 is implemented by an SSD, an HDD, or the like, for example. The storage device 310 is communicably connected to the information processing device 320 via the network 330. The communication unit 313 includes a communication interface that is communicable with the information processing device 320, the control device 3, a video processing device 302 described later, and an operation room camera 301 described later (see FIG. 9) on the basis of a predetermined communication standard such as Ethernet or Wi-Fi, for example.

The information processing device 320 includes a control unit 321, a storage unit 322, and a communication unit 323. The control unit 321 is implemented by a CPU, for example. The control unit 321 executes a computer program stored in the storage unit 322, thereby controlling the hardware components of the information processing device 320, and executing various processing. The storage unit 322 is implemented by an SSD, an HDD, or the like, for example. The communication unit 323 includes a communication interface that is communicable with the storage device 310 and an observation terminal 340 (see FIG. 10) on the basis of a predetermined communication standard such as Ethernet or Wi-Fi, for example.

Figure 9:
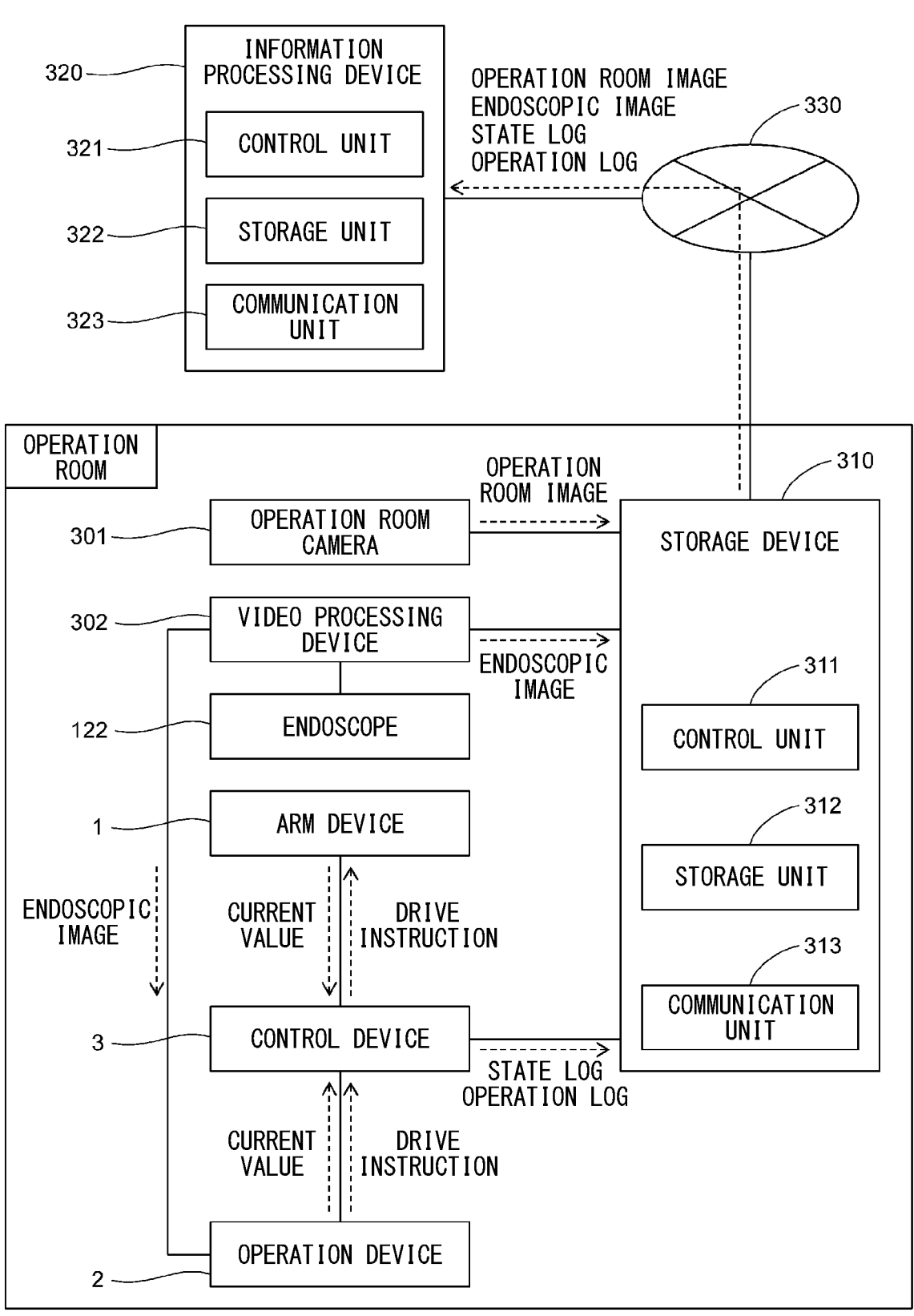
FIG. 9 shows outlines of connection between the surgical robot, the information processing system, and the like, and information exchanged between devices, according to the embodiment.

FIG. 9 shows the outlines of connection between the surgical robot 4, the information processing system 5, and the like, and information exchanged between the devices.

In the operation room, the arm device 1, the operation device 2, the control device 3, the endoscope 122 attached to the arm device 1, the video processing device 302 for processing a video captured by the endoscope 122, the operation room camera 301 for capturing an image of the entire operation room, and the storage device 310, are arranged. The control device 3, the video processing device 302, and the operation room camera 301 are communicably connected to the storage device 310. The information processing device 320 is installed in, for example, a cloud environment outside the operation room, and is communicably connected to the storage device 310.

The operation device 2 and the storage device 310 may not necessarily be installed in the operation room, and may be installed in another room inside the facility.

In response to a request from the storage device 310, the operation room camera 301 transmits the captured video (operation room image) to the storage device 310. The endoscope 122 is connected to the video processing device 302. The video processing device 302 transmits the video (endoscopic image) captured by the endoscope 122 to the operation device 2. In response to a request from the storage device 310, the video processing device 302 transmits the endoscopic image captured by the endoscope 122 to the storage device 310. The operation device 2 displays the endoscopic image received from the video processing device 302 on the viewer 211 (see FIG. 3).

As described above, the operator who is a doctor operates the operation device 2 to drive the arm device 1, thereby performing the surgery.

At this time, the operation device 2 transmits a drive instruction based on a generated output to the control device 3, according to an operation of the operator in real time, i.e., each time any of the encoders 261, 271 to 276 and the limit sensors 281 to 287 (see FIG. 12) generates an output. In addition, the operation device 2 transmits a current value indicating the state, of the operation target of the operation device 2, which changes according to the operation of the operator, to the control device 3 at predetermined time intervals (e.g., 1 second intervals). In response to a request from the storage device 310, the control device 3 transmits, to the storage device 310, a state log generated from a plurality of current values received from the operation device 2. The control device 3 converts the drive instruction received from the operation device 2 to a drive instruction for the arm device 1, and transmits, to the arm device 1, the converted drive instruction in real time, i.e., each time the control device 3 receives the drive instruction from the operation device 2. Thus, the arm device 1 is operated according to the operation of the operator to the operation device 2. The arm device 1 transmits, to the control device 3, the current values indicating the motions of the arms 111 to 114 and the like at predetermined time intervals (e.g., 1 second intervals). In response to a request from the storage device 310, the control device 3 transmits, to the storage device 310, an operation log generated from the current values received from the arm device 1.

The storage device 310 stores the state log and the operation log received from the control device 3 into the storage unit 312. In addition, the storage device 310 stores the video (operation room image) received from the operation room camera 301 and the video (endoscopic image) received from the video processing device 302, into the storage unit 312. Reception of the operation room image, the endoscopic image, the state log, and the operation log is continued for a predetermined time period, e.g., from when the use of the operation room for the surgery is started to when the use is ended. The storage device 310 transmits the operation room image, the endoscopic image, the state log, and the operation log stored in the storage unit 312 to the information processing device 320 in real time.

The control unit 311 of the storage device 310 may process the operation room image stored in the storage unit 312, according to need. For example, the control unit 311 may perform a blurring process on a person included in the operation room image, and information that may lead to personal information of the patient, to prevent the person and the personal information from being specified.

The information processing device 320 stores the operation room image, the endoscopic image, the state log, and the operation log received from the storage device 310, into the storage unit 322. In response to a request from the observation terminal 340 (see FIG. 10), the information processing device 320 generates a surgical image including the operation room image, the endoscopic image, a reconstructed image based on the state log, and a reconstructed image based on the operation log, and transmits the surgical image to the observation terminal 340.

For an observer who is going to learn how to operate the operation device 2, just watching the operation of the skilled operator (expert) beside the operation device 2 is difficult to satisfactorily learn the operation. For example, if the view of the operation target (the operation part 221 or the foot pedals 231 to 237) is obstructed by a part of the operation device 2, the observer cannot grasp how the operation is actually performed. If a plurality of operation targets are simultaneously operated, the observer should keep the plurality of operation targets in sight, which makes it difficult to grasp the plurality of operations.

Moreover, if the pair of movable plates 221b of the operation part 221 are slightly opened and closed, it is difficult for the observer to grasp the degree of the operation by just watching the operation part 221. In addition, if the feet of the operator are positioned above or in front of the foot pedals 231 to 237, the observer cannot grasp the preparation state by just watching the operation room image and the endoscopic image.

Meanwhile, in the present embodiment, the surgical image including the operation room image, the endoscopic image, the reconstructed image based on the state log, and the reconstructed image based on the operation log is transmitted to the observation terminal 340 (see FIG. 10) used by the observer. The reconstructed image based on the state log includes an image visualizing an operation of the operator to the operation target of the operation device 2. The image visualizing the operation of the operator to the operation target of the operation device 2 is displayed on a display unit 343 of the observation terminal 340. The observer refers to this image together with an image showing the motion of the surgical robot 4 (the arm device 1 and/or the operation device 2) and/or the motions of the surgical instruments 121 to 124, thereby learning the motion of the surgical robot 4 or the surgical instruments 121 to 124, and the operation to the operation target for realizing the motion.

Figure 10:
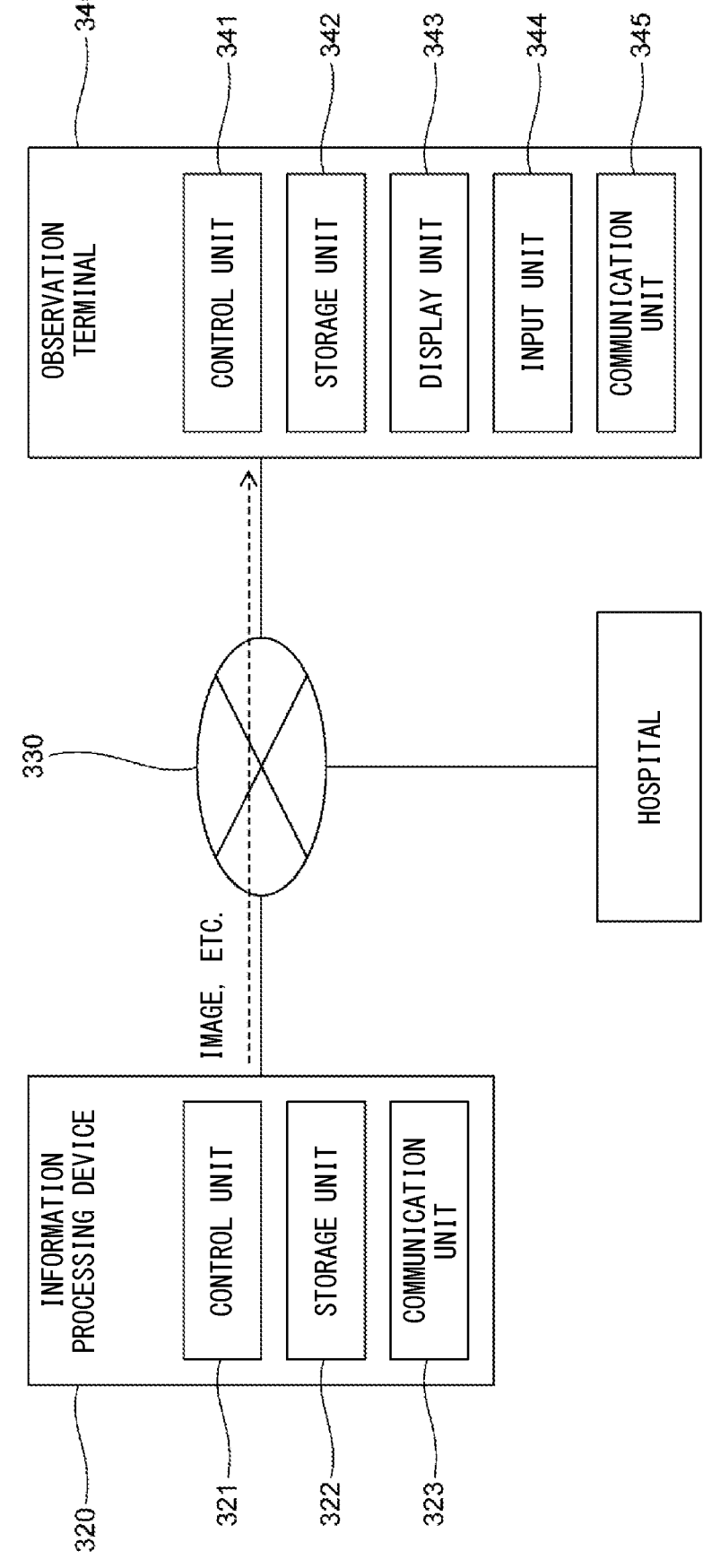
FIG. 10 is a block diagram showing a use mode of an information processing device according to the embodiment.

FIG. 10 is a block diagram showing a use mode of the information processing device 320.

The observation terminal 340 is a computer that is operated by the observer who is going to learn the operation of the operation device by the expert. The observation terminal 340 includes a control unit 341, a storage unit 342, a display unit 343, an input unit 344, and a communication unit 345.

The control unit 341 is implemented by a CPU, for example. The control unit 341 executes a computer program stored in the storage unit 342, thereby controlling the hardware components of the observation terminal 340, and executing various processing. The storage unit 342 is implemented by an SSD, an HDD, or the like, for example. The display unit 343 is implemented by a liquid crystal display, for example. The input unit 344 is implemented by a keyboard and a mouse, for example. The display unit 343 and the input unit 344 may be implemented by a touch-panel type display. The communication unit 345 includes a communication interface that is communicable with the information processing device 320 on the basis of a predetermined communication standard such as Ethernet or Wi-Fi, for example.

The control unit 341 of the observation terminal 340 executes a web browser or a predetermined application to obtain the surgical image for learning the operation of the operation device 2 from the information processing device 320. Then, the control unit 341 displays the obtained surgical image on the display unit 343. The observer refers to the surgical image displayed on the display unit 343, and learns the operation of the operation device 2 by the operator who is a doctor. The surgical image displayed on the display unit 343 will be described later with reference to FIG. 17 and subsequent figures.

Figure 11:
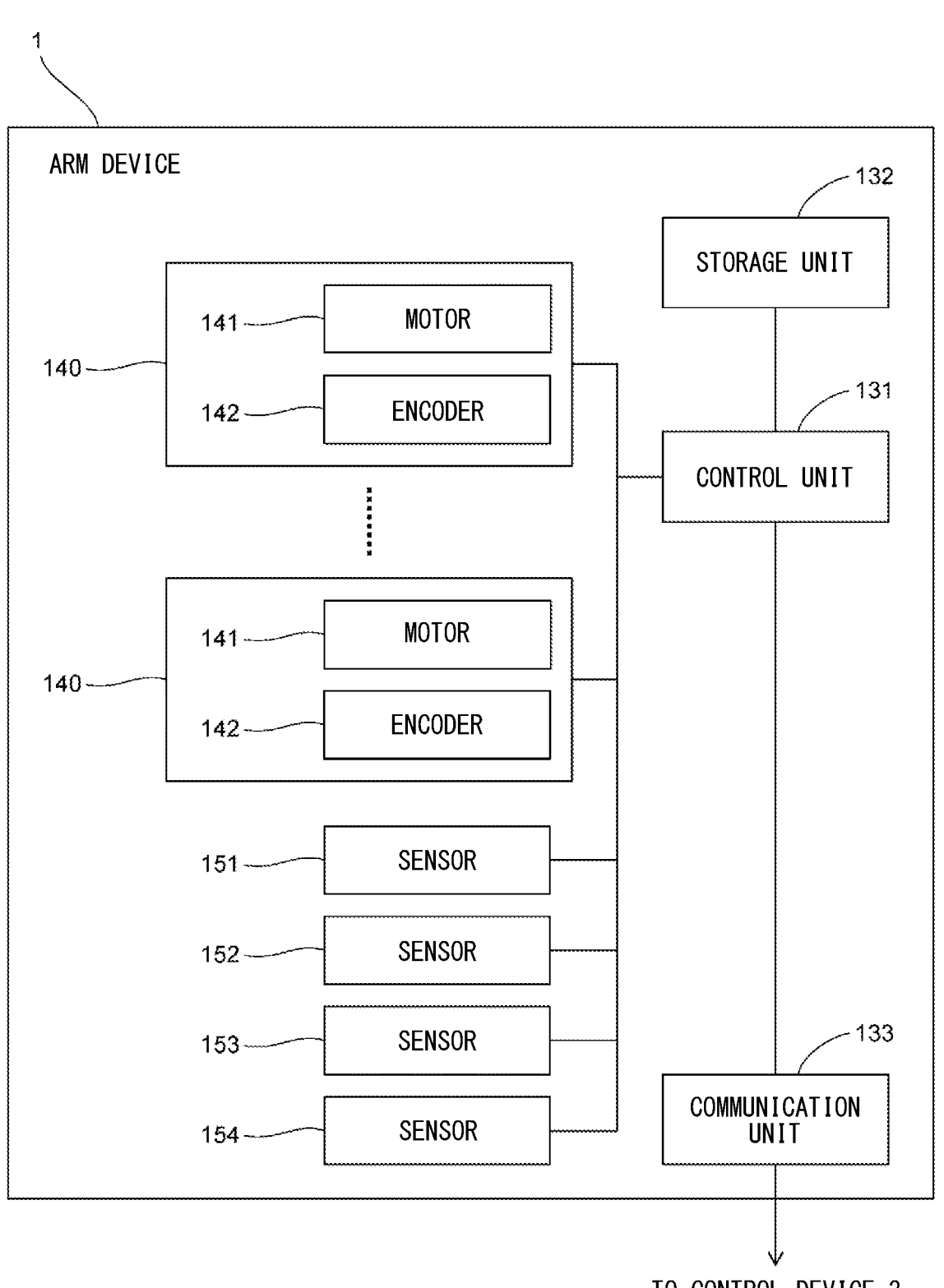
FIG. 11 is a block diagram showing a configuration of an arm device according to the embodiment.

FIG. 11 is a block diagram showing the configuration of the arm device 1.

The arm device 1 includes a control unit 131, a storage unit 132, a communication unit 133, a plurality of operating units 140, and sensors 151 to 154.

The control unit 131 is implemented by an FPGA or a CPU, for example. The storage unit 132 is implemented by a ROM or a RAM, for example. The communication unit 133 includes a communication interface that is communicable with the control device 3 on the basis of a predetermined communication standard.

The operating units 140 correspond to the operating parts of the base arm 103 and the arms 111 to 114 of the arm device 1. An operating unit 140 corresponds to one joint of an arm, for example. Each operating unit 140 includes a motor 141 and an encoder 142. The motor 141 is a stepping motor. The encoder 142 outputs a driving amount of the motor 141. The encoders 142 are disposed one by one at the ends of the twelve links of each of the arms 111 to 114.

The sensors 151 to 154 are disposed on the arms 111 to 114, and detect attachment/detachment of the surgical instruments to/from the arms 111 to 114, respectively. For example, each of the sensors 151 to 154 may be a sensor that detects electrical connection of the surgical instrument to the arm, or may be a photoelectric sensor that detects physical attachment/detachment of the surgical instrument to/from the arm.

The surgical instruments attached to the arm device 1 are given names and serial numbers. When the surgical instruments are attached to the arms 111 to 114, the control unit 131 stores, in the storage unit 132, the names and the serial numbers given to the surgical instruments.

On the basis of the drive instruction (see FIG. 9) received from the control device 3 via the communication unit 133, the control unit 131 drives the motor 141 of the corresponding operating unit 140. In addition, the control unit 131 transmits the current values constituting the operation log based on the output values of the encoders 142, detection signals of the sensors 151 to 154, and the names and the serial numbers of the surgical instruments 121 to 124, to the control device 3 via the communication unit 133. The operation log, the detection signals of the sensors 151 to 154, and the names and the serial numbers of the surgical instruments 121 to 124 are transmitted from the control device 3 to the information processing device 320 via the storage device 310, and are stored in the storage unit 322 of the information processing device 320.

Figure 12:
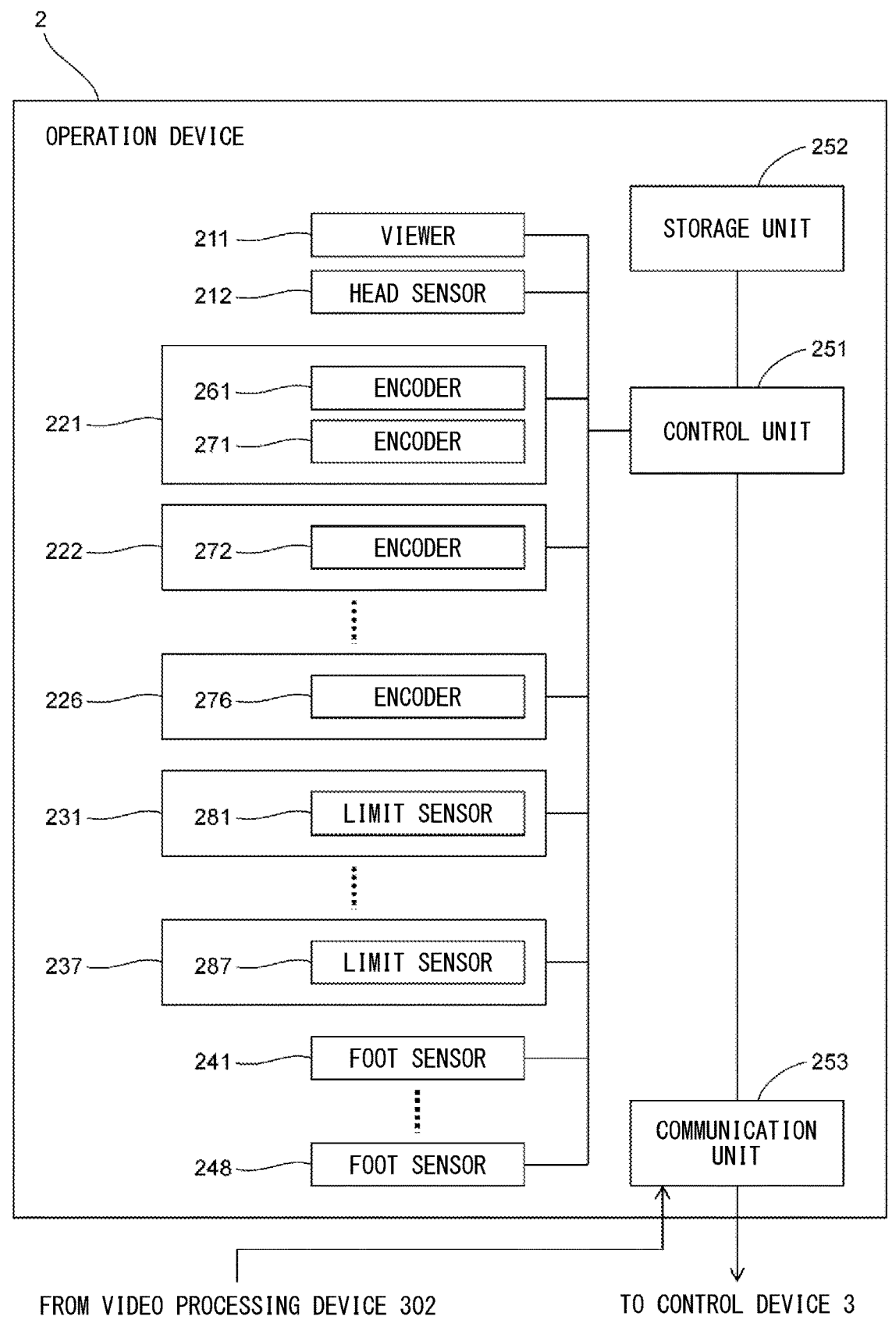
FIG. 12 is a block diagram showing a configuration of the operation device according to the embodiment.

FIG. 12 is a block diagram showing the configuration of the operation device 2.

The operation device 2 includes a control unit 251, a storage unit 252, a communication unit 253, the viewer 211, the head sensor 212, the operation part 221, the movable parts 222 to 226, the foot pedals 231 to 237, and the foot sensors 241 to 248. FIG. 12 shows the configuration of one of the left and right hand controllers 220, for convenience.

The control unit 251 is implemented by an FPGA or a CPU, for example. The storage unit 252 is implemented by a ROM or a RAM, for example. The communication unit 253 includes a communication interface capable of communicating with the endoscope 122 and the control device 3 on the basis of a predetermined communication standard.

The operation part 221 includes the encoders 261, 271. The movable parts 222 to 226 include the encoders 272 to 276, respectively. The foot pedals 231 to 237 include the limit sensors 281 to 287, respectively. Each of the encoders 261, 271 to 276 outputs an amount of movement or rotation of the corresponding part.

Specifically, the encoder 261 of the operation part 221 outputs an amount of pushing the pair of movable plates 221b (see FIG. 4) of the operation part 221. The encoders 271 to 276 respectively output an amount of rotation between the operation part 221 and the movable part 222, an amount of rotation between the movable parts 222 and 223, an amount of rotation between the movable parts 223 and 224, an amount of rotation between the movable parts 224, 225, an amount of rotation between the movable parts 225, 226, and an amount of rotation between the movable part 226 and the support member 202 (see FIG. 3). The limit sensors 281 to 287 respectively detect whether or not the foot pedals 231 to 237 are stepped on. The detection signals of the limit sensors 284 to 287 are information indicating switching between energization and non-energization by the foot pedals 234 to 237, respectively.

The control unit 251 displays the endoscopic image received from the video processing device 302 on the viewer 211. The control unit 251 transmits the current values that constitute the state log based on the output values of the encoders 261, 271 to 276 and the detection signals of the limit sensors 281 to 287, to the control device 3 via the communication unit 253. The state log is transmitted from the control device 3 to the information processing device 320 via the storage device 310, and is stored in the storage unit 322 of the information processing device 320.

FIG. 13 illustratively shows the current values constituting the state log transmitted from the operation device 2 to the control device 3. The state log is information in which the current values as shown in FIG. 13 are stored at predetermined intervals for a predetermined time period together with the current time.

The example shown in FIG. 13 includes, as the current values indicating the current states of the respective parts, the output values of the encoders 261, 271 to 276 corresponding to the left and right hand controllers 220, an angle between the pair of movable plates 221b that is calculated from the output value of the encoder 261 corresponding to the left operation part 221, and an angle between the pair of movable plates 221b that is calculated from the output value of the encoder 261 corresponding to the right operation part 221. The angle between the pair of movable plates 221b is calculated by the control unit 251 of the operation device 2.

In FIG. 13, the current values of 1_1 link to 1_7 link of the hand controller (right) indicate the output values of the encoders 271 to 276 disposed at the ends of the seven links included in the right hand controller 220. The current value of 1_grip angle of the hand controller (right) indicates an angle between the pair of movable plates 221b that is calculated from the output value of the encoder 261 corresponding to the right operation part 221. Likewise, the current values of 1_1 link to 1_7 link of the hand controller (left) indicate the output values of the encoders 271 to 276 disposed at the ends of the seven links included in the left hand controller 220. The current value of 1_grip angle of the hand controller (left) indicates an angle between the pair of movable plates 221b that is calculated from the output value of the encoder 261 corresponding to the left operation part 221. The current values constituting the state log also include the detection signals of the limit sensors 281 to 287 corresponding to the foot pedals 231 to 237, the detection signals of the foot sensors 241 to 248, and the detection signal of the head sensor 212.

The control unit 251 of the operation device 2 transmits the current values at 1-second intervals, for example, to the control device 3. The control device 3 stores, as the state log, a set of the plurality of current values received and a plurality of current times corresponding to the current values, into the storage unit 32.

FIG. 14 shows an example of the state log. FIG. 14 shows the state log of the angle between the pair of movable plates 221b that is calculated from the output values of the encoder 261 corresponding to the left operation part 221, and includes the current time in 1-second intervals within a predetermined time period, and the current values (angles) at the respective current times.

FIG. 15 illustratively shows the current values constituting the operation log transmitted from the arm device 1 to the control device 3. The operation log is information in which the current values as shown in FIG. 15 are stored at predetermined intervals for a predetermined time period together with the current time. FIG. 15 shows the current values corresponding to the parts of the arm 111 and some of the parts of the arm 112, for convenience.

In FIG. 15, the current values of 1_1 link to 1_12 link of an operation arm 1 indicate the output values of the encoders 142 disposed at the ends of the twelve links included in the arm 111, respectively. Likewise, the current values of 2_1 link to 2_12 link of an operation arm 2 indicate the output values of the encoders 142 disposed at the ends of the twelve links included in the arm 112 (in FIG. 15, the current values of 2_5 link to 2_12 link are omitted).

Upon receiving a drive instruction from the operation device 2, the control device 3 converts the received drive instruction into a drive instruction for the arm device 1, and transmits the drive instruction to the arm device 1. The arm device 1 drives the respective motors 141 on the basis of the received drive instruction.

The current values constituting the operation log include, as the current values of the respective parts, the output values of the encoders 142 that indicate the amounts of operations of the motors 141 operated based on the drive instruction.

The control unit 131 of the arm device 1 transmits the current values at 1-second intervals, for example, to the control device 3. The control device 3 stores, as the operation log, a set of the plurality of current values received and a plurality of current times corresponding to the current values, into the storage unit 132.

FIG. 16 shows an example of the operation log. FIG. 16 shows the operation log of the operation amount of a motor at a predetermined movable part of the arm 111, and includes the current time in 1-second intervals within a predetermined time period, and the current values (operation amounts) at the current times.

Next, an image displayed on the display unit 343 of the observation terminal 340 (see FIG. 10) will be described.

Upon receiving instruction information from the observation terminal 340, the control unit 321 of the information processing device 320 transmits, to the observation terminal 340, the endoscopic image and the operation room image stored in the storage unit 322, generates various images and information based on the state log and the operation log stored in the storage unit 322, and transmits the images and information to the observation terminal 340. The observation terminal 340 displays, on the display unit 343, a surgical image 400 including the endoscopic image, the operation room image, and the various information based on the state log and the operation log. Display of the surgical image 400 on the display unit 343 of the observation terminal 340 may be performed by so-called download reproduction in which images and information over the entire period are received from the information processing device 320 and thereafter display is started, or so-called streaming reproduction in which images and information are displayed while being received from the information processing device 320.

The images displayed on the display unit 343 are not limited to the images transmitted from the information processing device 320 to the observation terminal 340. The images displayed on the display unit 343 may be images that are generated by the control unit 341 of the observation terminal 340 on the basis of the state log and the operation log received from the information processing device 320.

Figure 17:
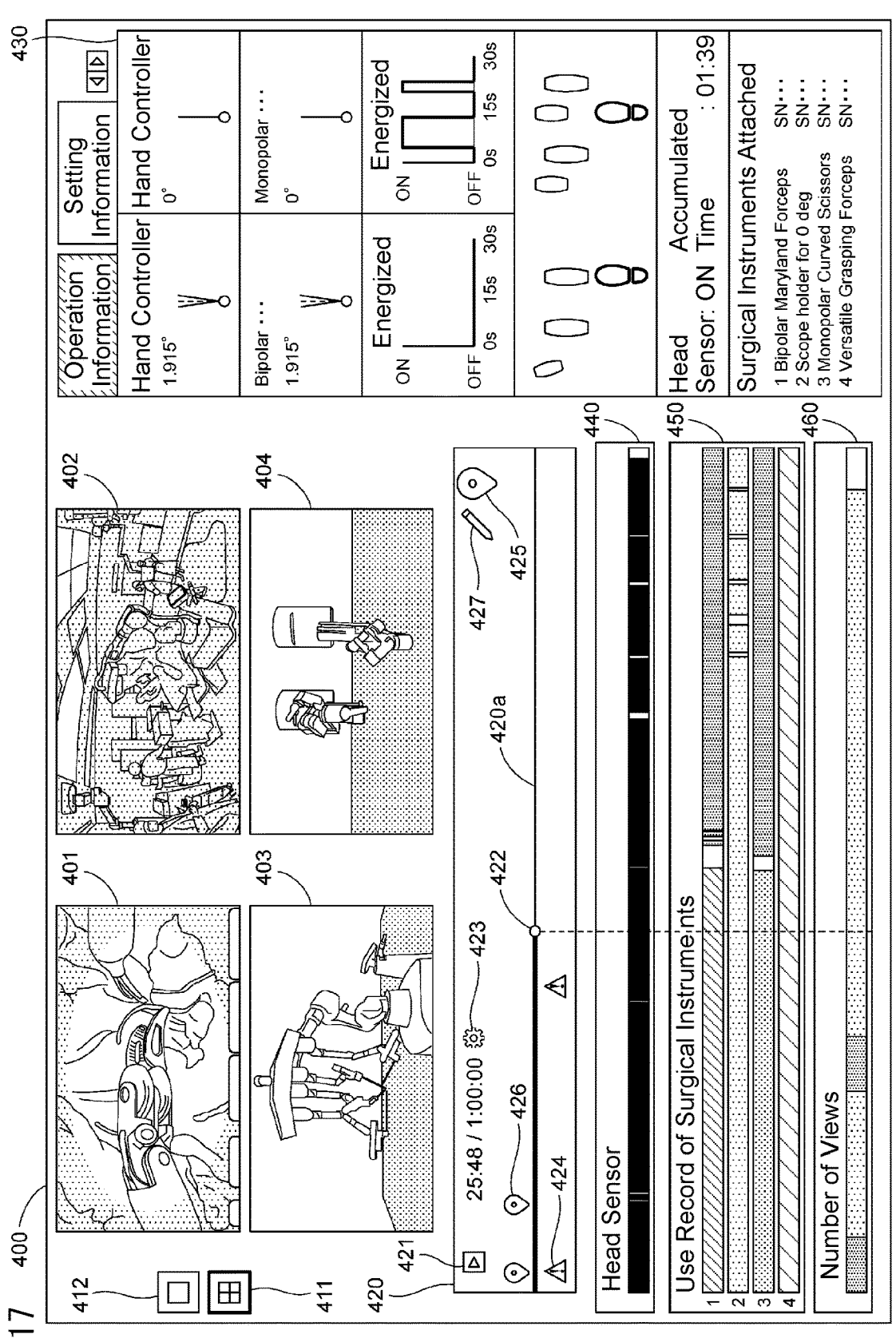
FIG. 17 schematically shows a configuration of a surgical image according to the embodiment.

FIG. 17 schematically shows the configuration of the surgical image 400.

The surgical image 400 includes an endoscopic image 401, an operation room image 402, schematic images 403, 404, display switching buttons 411, 412, a moving image control area 420, and an information display area 430. The surgical image 400 further includes an image 440 indicating information on the head sensor 212, an image 450 indicating the use record of surgical instruments, and an image 460 indicating the number of views. The images 440, 450, and 460 will be described later with reference to FIG. 20.

As shown in FIG. 17, the endoscopic image 401, the operation room image 402, and the schematic images 403, 404 are moving images. The schematic image 403 is a moving image in which the operating states of the parts of the arm device 1 are three-dimensionally configured based on the operation log of the arm device 1. The schematic image 404 is a moving image in which the operating state of the hand controller 220 of the operation device 2 is three-dimensionally configured based on the state log of the operation device 2. These four moving images are synchronized with each other, and indicate the states at the same time.

Figure 18:
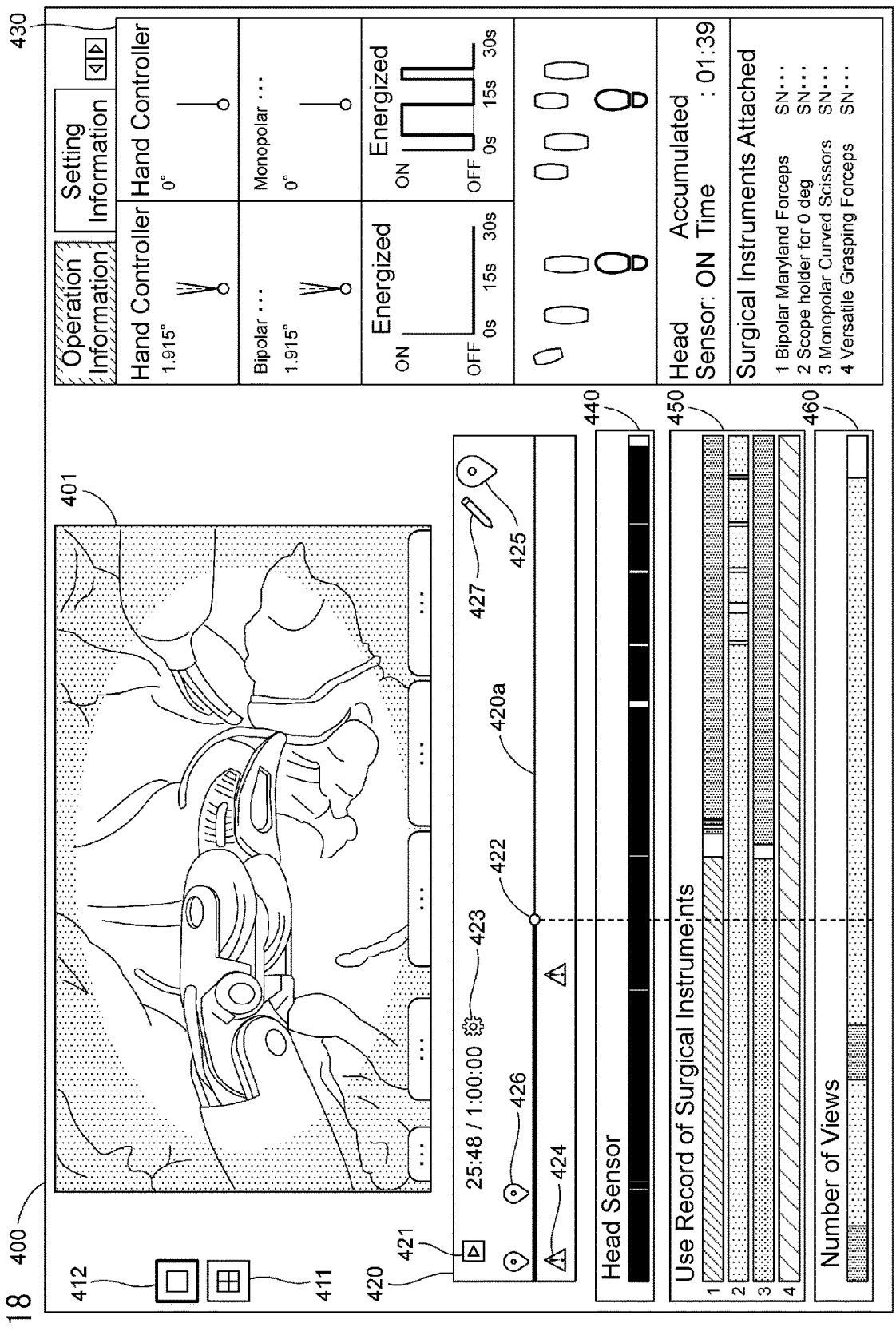
FIG. 18 schematically shows the configuration of the surgical image according to the embodiment.

The display switching buttons 411, 412 are buttons for switching between a mode in which the four moving images (the endoscopic image 401, the operation room image 402, and the schematic images 403, 404) are displayed side by side, and a mode in which one of the four moving images is enlarged and displayed. When the display switching button 411 is operated, the four moving images are displayed side by side as shown in FIG. 17. When the display switching button 412 is operated, one moving image is enlarged and displayed as shown in FIG. 18.

When the display switching button 411 is operated, a screen for setting the positions of the four moving images is displayed. Through setting on this screen, the four moving images can be displayed at desired positions as shown in FIG. 17. When the display switching button 412 is operated, a screen for setting which one of the four moving images should be disposed, is displayed. Through setting on this screen, a desired one of the four moving images is displayed as shown in FIG. 18.

Figure 19:
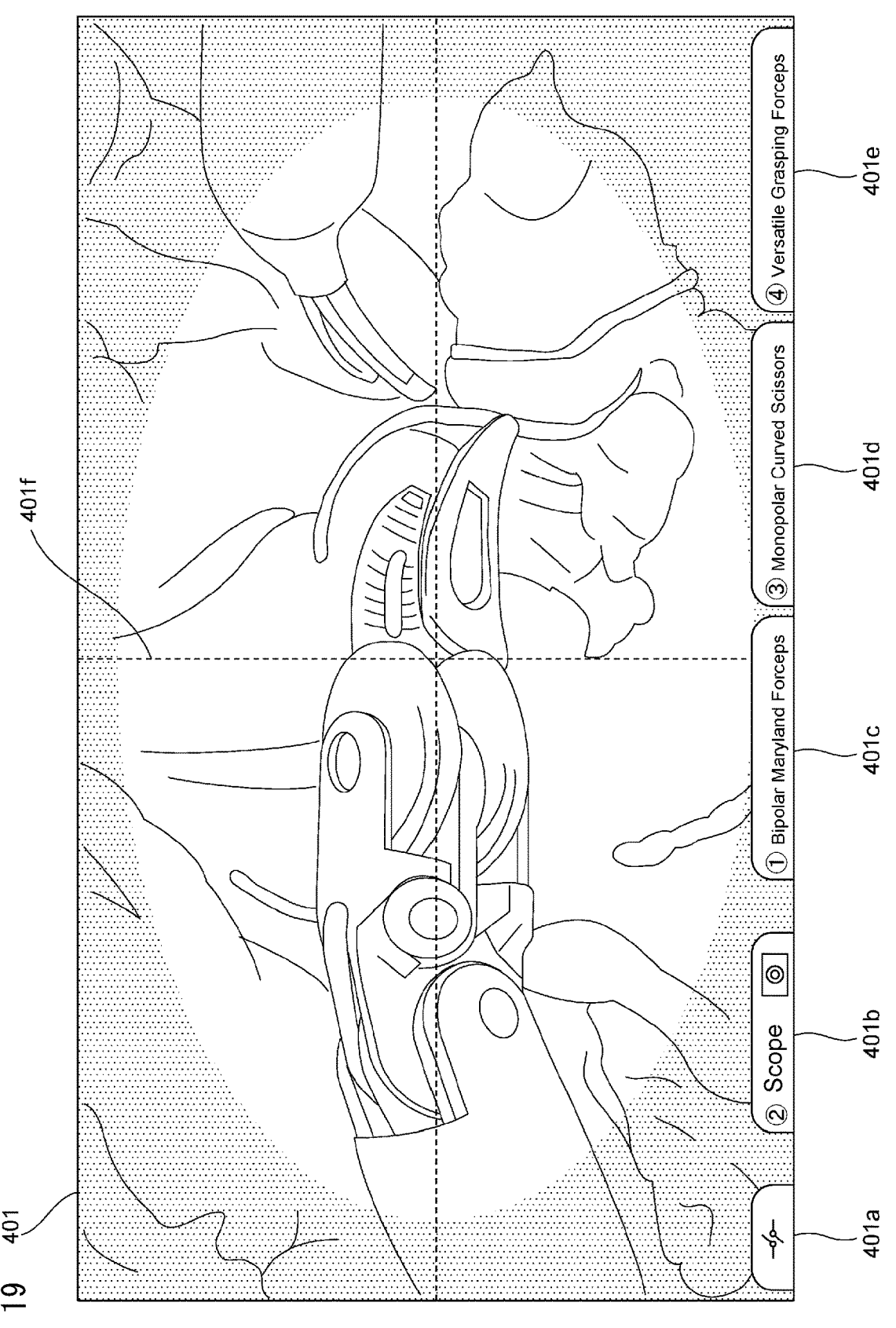
FIG. 19 is an enlarged view schematically showing a configuration of an endoscopic image according to the embodiment.

FIG. 19 is an enlarged view schematically showing the configuration of the endoscopic image 401.

In the endoscopic image 401, display areas 401a to 401e indicating information on the surgical instruments 121 to 124 attached to the arms 111 to 114 of the arm device 1 are displayed together with the image captured by the endoscope 122. The endoscopic image 401 is the same image as the image displayed on the viewer 211 of the operation device 2.

The display area 401a shows the operation state of the foot pedal 232 being a clutch pedal. When the foot is positioned on the foot pedal 232, a color is given to the periphery of the display area 401a. When the foot pedal 232 is stepped on, the color is given to the inside of the display area 401a. The display area 401b shows the operation state of the foot pedal 233 for operating the arm to which the endoscope 122 is attached. When the foot is positioned on the foot pedal 233, a color is given to the periphery of the display area 401b. When the foot pedal 233 is stepped on, the color is given to the inside of the display area 401b.

The display area 401c shows the operation states of the foot pedals 234, 235 for operating the forceps (electrocautery). When the foot is positioned on the foot pedal 234 or 235, a color is given to the periphery of the display area 401c. When the foot pedal 234 is stepped on, a first color is given to the inside of the display area 401c. When the foot pedal 235 is stepped on, a second color is given to the inside of the display area 401c. For example, the first color is light blue and the second color is yellow.

The display area 401d shows the operation states of the foot pedals 236, 237 for operating the forceps (electrocautery), and the display area 401e shows the operation states of the foot pedals 236, 237 for operating other forceps (electrocautery). As described above, each time the foot pedal 231 is stepped on, the target of the foot pedal 236, 237 is switched between the forceps 123, 124. When the foot is positioned on the foot pedal 236 or 237, a color is given to the periphery of the target display area out of the display areas 401d, 401e. When the foot pedal 236 is stepped on, the first color is given to the inside of the target display area out of the display areas 401d, 401e. When the foot pedal 237 is stepped on, the second color is given to the inside of the target display area out of the display areas 401d, 401e.

In the display areas 401c to 401e, for example, the names of the surgical instruments 121, 123, 124 attached to the arms 111, 113, 114 are displayed as information on these surgical instruments. Whether or not the respective surgical instruments are attached and the names of the surgical instruments are generated based on the detection signals of the sensors 151 to 154, and the names and the serial numbers, of the surgical instruments 121 to 124, obtained at the time of attachment to the arms 111 to 114.

By referring to the display areas 401a to 401e in the endoscopic image 401, the observer can grasp the operation states of the foot pedals 232 to 237, and can grasp what surgical instruments are attached to the arms 111 to 114.

As shown in FIG. 19, division lines 401f that divide the endoscopic image 401 into four areas may be displayed in the endoscopic image 401. Using the four areas divided by the division lines 401f as guides, the observer refers to the areas in which the respective surgical instruments are positioned, whereby the observer can learn how the surgical instruments should be arranged and how the surgical instruments should be moved, according to the condition of the surgery.

Referring back to FIG. 17, the moving image control area 420 includes a play button 421, a play position mark 422, a play speed setting button 423, a warning mark 424, a bookmark insertion button 425, a bookmark 426, and an editing start button 427.

When the play button 421 is operated, the endoscopic image 401, the operation room image 402, and the schematic images 403, 404 are played or paused.

The play position mark 422 is a mark indicating a play position of the endoscopic image 401, the operation room image 402, and the schematic images 403, 404 on a time line 420a. The play position can be changed by operating the play position mark 422. When the play speed setting button 423 is operated, a sub menu is opened, and the play speed can be set in the sub menu. The warning mark 424 indicates a position on the time line 420a where an event requiring warning to the observer occurs, e.g., a position on the time line 420a where an error occurs in the surgical robot 4.

When the bookmark insertion button 425 is operated, a bookmark 426 is added to the position of the play position mark 422. In addition, a screenshot of the surgical image 400 at the time of the operation of the bookmark insertion button 425 is stored in the storage unit 322 of the information processing device 320. Storage of the screenshot of the surgical image 400 will be described later with reference to FIG. 25.

When the editing start button 427 is operated, the observer can write characters and figures in the surgical image 400 by performing operations such as clicking and dragging on the surgical image 400. When the bookmark insertion button 425 is operated in this state, the screenshot of the surgical image 400 is stored in the storage unit 322 of the information processing device 320 together with the characters and figures written in the surgical image 400. The editing start button 427 enabling writing of characters and figures on the surgical image 400 will be described later with reference to FIG. 26.

Figure 20:
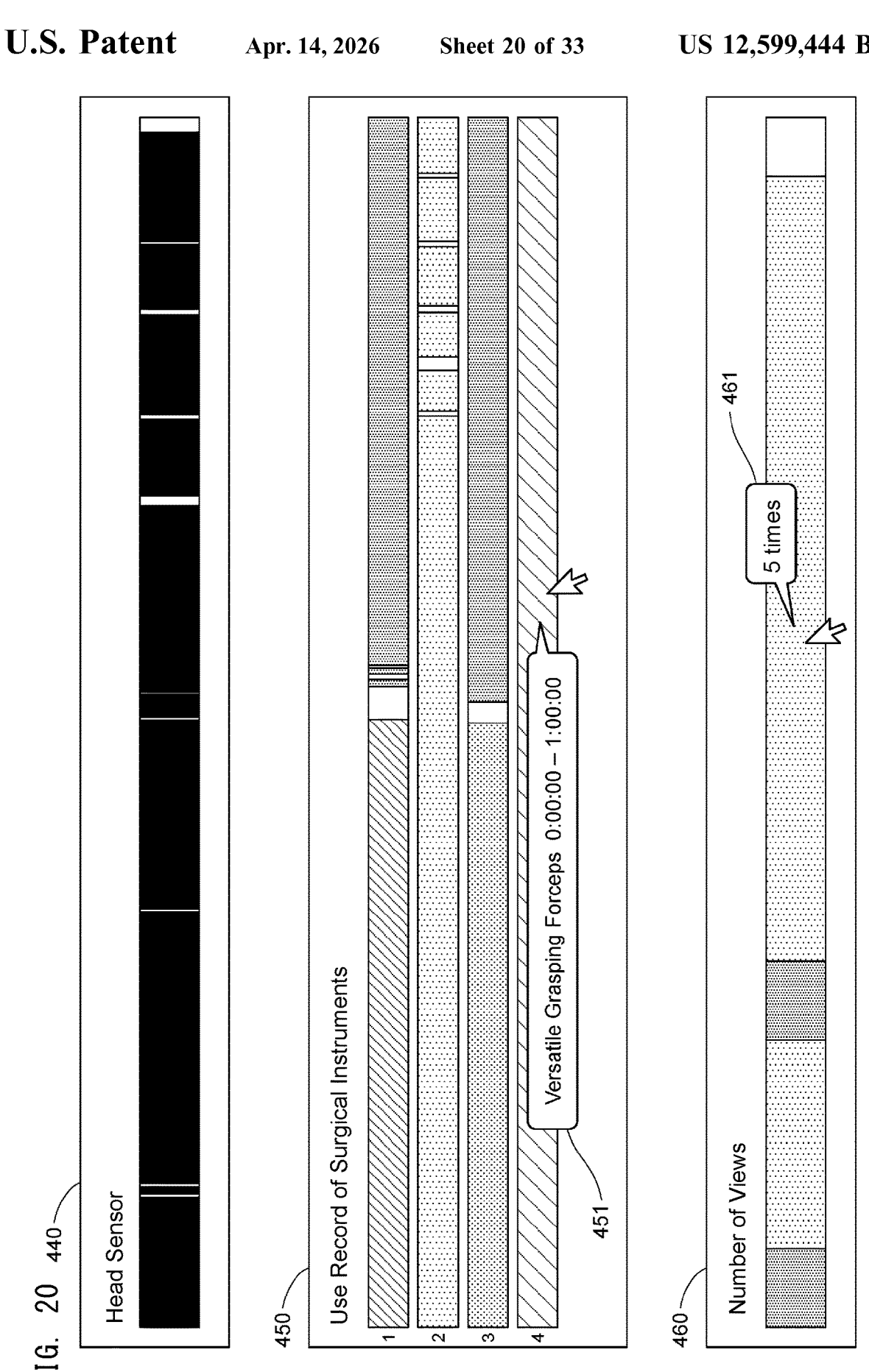
FIG. 20 schematically shows configurations of images and the like showing a use record of surgical instruments, according to the embodiment.

FIG. 20 schematically shows the configurations of the images 440, 450, and 460 displayed in the surgical image 400.

Each of band areas in the images 440, 450, and 460 corresponds to the time line 420a in the moving image control area 420 shown in FIG. 17.

The band area of the image 440 indicating information on the head sensor 212 includes portions displayed in black and portions displayed in white. Each of the black portions indicates the state where the head sensor 212 detects the operator looking into the viewer 211, i.e., detects the operator being close to the viewer 211. Each of the white portions indicates the state where the head sensor 212 detects the operator not looking into the viewer 211, i.e., does not detect the operator being close to the viewer 211.

The image 450 showing the use record of the surgical instruments includes band areas numbered 1 to 4. The band areas 1 to 4 correspond to the arms 111 to 114, respectively. Hatched portions in the band areas indicate the kinds and the attachment periods of the forceps and the endoscope attached to the arms 111 to 114. In the example shown in FIG. 20, the band areas 1, 3 indicate that the forceps attached to the arms 111, 113 were replaced during the surgery. The band area 2 indicates that the endoscope 122 attached to the arm 112 was detached several times near the end of the surgery. The reason is because the endoscope 122 was detached from the arm 112 to defog the head of the endoscope 122. The band area 4 indicates that the forceps 124 attached to the arm 114 were not detached.

When a cursor of a mouse or the like is placed on a band area in the image 450, surgical instrument information 451 is displayed as shown in the band area 4. The surgical instrument information 451 includes the name of the forceps or the endoscope that was attached at the time position where the cursor is placed, and a time period in which the forceps or the endoscope was used.

The band area of the image 460 showing the number of views includes portions having different concentrations. Each concentration indicates the number of views of the observer at the corresponding position. For example, a portion displayed in white indicates that the number of views of the observer at this position is 0. As the concentration increases by one stage, the number of views is increased by a predetermined number of times.

When the cursor of the mouse or the like is placed on the band area in the image 460, number-of-views information 461 indicating the number of views at the time position where the cursor is placed is displayed.

Figure 21:
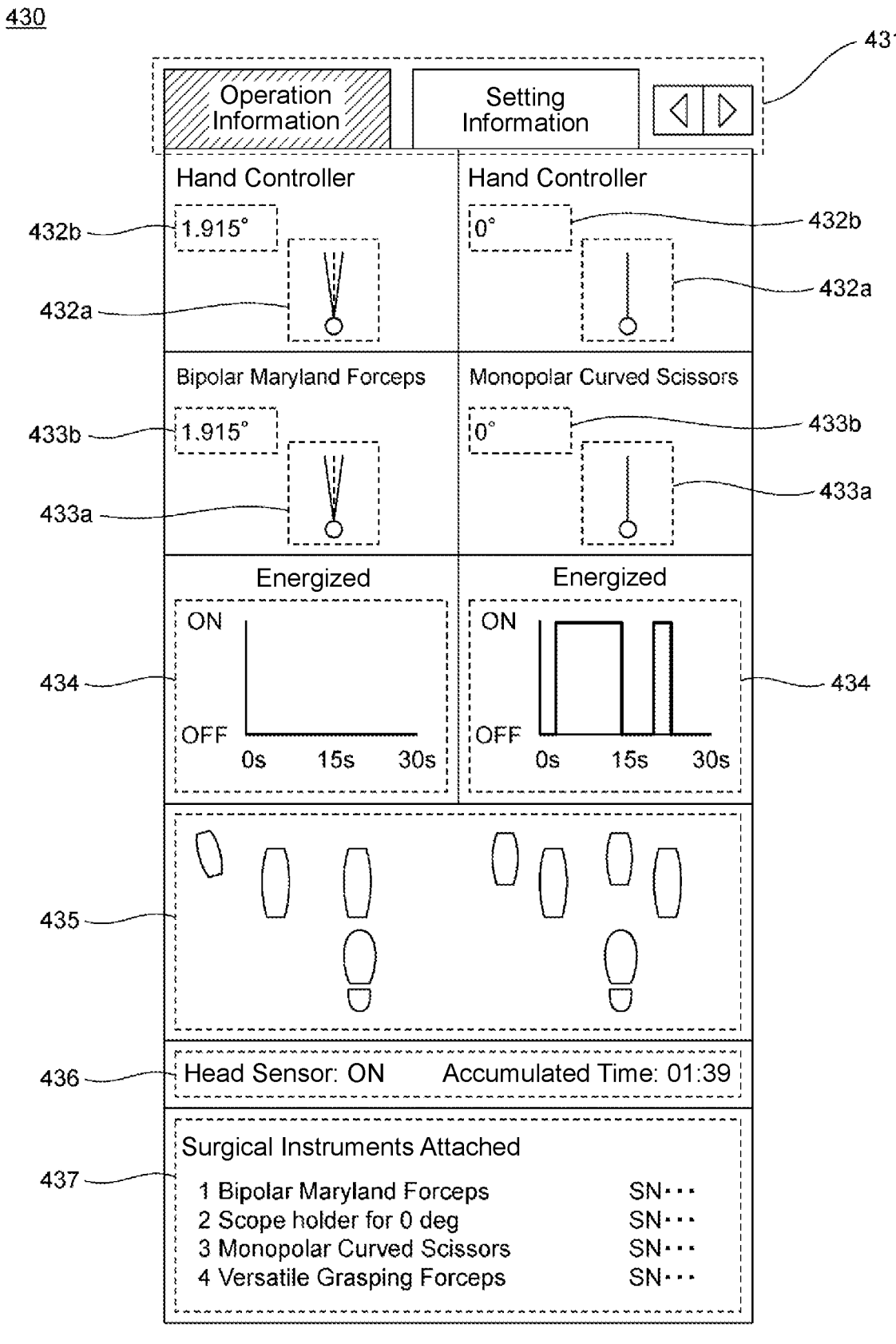
FIG. 21 is an enlarged view schematically showing a configuration of an information display area according to the embodiment.

FIG. 21 is an enlarged view schematically showing the configuration of the information display area 430 in the case where an operation information tab is selected.

The contents of the information display area 430 are displayed in synchronization with the play positions of the endoscopic image 401, the operation room image 402, and the schematic images 403, 404.

When the operation information tab is being selected, the information display area 430 includes a display selection area 431, two images 432a, two images 432b, two images 433a, two images 433b, two images 434, and images 435 to 437. The images 432a, 432b, 433a, 433b, and 434 are disposed on the left and right of the information display area 430.

The left image 432a schematically shows the state of pushing the pair of movable plates 221b of the left hand controller 220, and the right image 432*a* schematically shows the state of pushing the pair of movable plates 221*b* of the right hand controller 220. The left image 432*b* shows an angle corresponding to the amount of pushing the pair of movable plates 221*b* of the left hand controller 220, and the right image 432*b* shows an angle corresponding to the amount of pushing the pair of movable plates 221*b* of the right hand controller 220. The images 432*a*, 432*b* are generated based on the state log. By referring to the images 432*a*, 432*b*, the observer can grasp the degree of opening/ closing of the pair of movable plates 221*b* of the operation part 221.

The left and right images 433*a* show the pinching states of the tips of the forceps operated by the left and right hand controllers 220, respectively. The left and right images 433*b* show angles corresponding to the pinching amounts of the forceps operated by the left and right hand controllers 220. The images 433*a*, 433*b* are generated based on the operation log. By referring to the images 433*a*, 433*b*, the observer can grasp the degree of opening/closing of the tips of the corresponding forceps.

The left image 434 shows a graph corresponding to the stepped-on state of the foot pedal 234, 235, and the right image 434 shows a graph corresponding to the stepped-on state of the foot pedal 236, 237. In the image 434, "ON" indicates the state where the foot pedals are stepped on, and "OFF" indicates the state where the foot pedals are not stepped on. The image 434 shows the stepped-on state for 30 seconds before the current time. The image 434 is generated based on the state log. By referring to the left image 434, the observer can grasp the timing and period in which the foot pedals 234, 235 were stepped on. By referring to the right image 434, the observer can grasp the timing and period in which the foot pedals 236, 237 were stepped on.

The image 435 schematically shows the positions of the feet of the operator on the foot unit 230, and the stepped-on states of the foot pedals 231 to 237. The image 435 is generated based on the state log.

FIGS. 22, 23 schematically show the configuration and transition of the image 435.

As shown in FIG. 22, the image 435 includes pedal images 471 to 477 corresponding to the foot pedals 231 to 237, and foot images 481 displayed according to the standby states of the feet.

The control unit 321 of the information processing device 320 determines whether each of the foot pedals 231 to 237 is in the hover state or the non-hover state on the basis of the detection signals of the foot sensors 241 to 248. As described above, the hover state includes the state where the feet are in front of the foot pedals, the state where the feet are above the foot pedals, and the state where the foot pedals are stepped on, and the non-hover state includes the state where the feet are not present in the foot unit 230. Based on the detection signals of the limit sensors 281 to 287, the control unit 321 determines whether or not each of the foot pedals 231 to 237 is stepped on. Then, the control unit 321 generates the image 435 on the basis of the determination result.

As shown in an upper stage of FIG. 22, when the left foot and the right foot are not positioned in the foot unit 230, the pedal images 471 to 477 are displayed in a normal frame-line thickness, and the foot images 481 are not displayed. From this, it is found that the feet are neither in the operating state nor in an operation preparing state with respect to the foot pedals 231 to 237.

In the state shown in the upper stage of FIG. 22, when the feet are positioned in front of or above the foot pedals, the foot images 481 are displayed as shown in a lower stage of FIG. 22. In the example shown in the lower stage of FIG. 22, the two foot images 481 are positioned in front of the pedal images 473, 475, respectively. From this, it is found that the left foot is positioned in front of or above the foot pedal 233 and the right foot is positioned in front of or above the foot pedal 235. In addition, it is found that the feet are in the operation preparing state with respect to the foot pedals 233, 235.

In the state shown in the lower stage of FIG. 22, when a foot pedal is stepped on, a color is given to the periphery of the corresponding pedal image as shown in an upper stage of FIG. 23. In the example shown in the upper stage of FIG. 23, the color is given to the periphery of the pedal image 477. From this, it is found that the foot pedal 237 is stepped on.

In the state shown in the upper stage of FIG. 23, when the foot pedal 233 is stepped on, a color is given to the periphery of the pedal image 473 as shown in a lower stage of FIG. 23. In the state shown in the lower stage of FIG. 23, since the right foot has moved out of the foot unit 230, the foot image 481 corresponding to the right foot is absent. From this, it is found that the right foot is not in the operation preparing state.

By referring to the pedal images 471 to 477 and the foot images 481 in the image 435, the observer can grasp the operating states and the operation preparing states with respect to the foot pedals 231 to 237.

Referring back to FIG. 21, an image 436 shows a detection result based on the head sensor 212, and an accumulated time, in which the operator has looked into the viewer 211, obtained by the head sensor 212. The image 436 is generated based on the state log. By referring to the image 436, the observer can grasp whether or not the operator is looking into the viewer 211 and how long (in total) the operator looks into the viewer 211 during the surgery.

An image 437 shows the names and the serial numbers of the surgical instruments 121 to 124 attached to the arms 111 to 114 of the arm device 1. The image 437 is generated based on the detection signals of the sensors 151 to 154, and the names and the serial numbers, of the surgical instruments 121 to 124, obtained at the time of attachment to the arms 111 to 114. By referring to the image 437, the observer can grasp the names and the serial numbers of the currently used surgical instruments 121 to 124.

Figure 24:
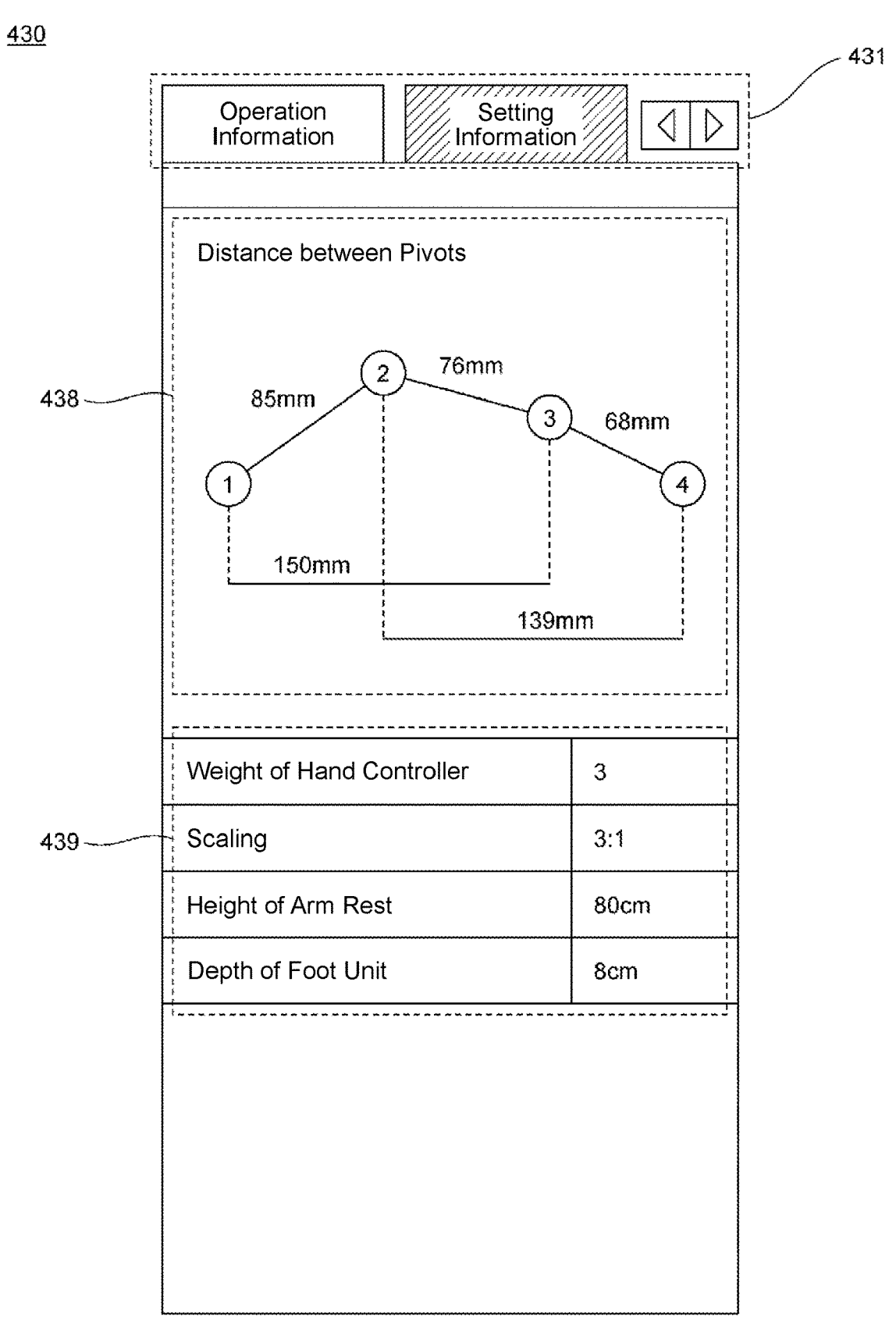
FIG. 24 is an enlarged view schematically showing the configuration of the information display area according to the embodiment.

FIG. 24 is an enlarged view schematically showing the configuration of the information display area 430 in the case where a setting information tab is selected.

In the case where the setting information tab is selected, the information display area 430 includes a display selection area 431, and images 438, 439.

The image 438 schematically shows pivot positions of the surgical instruments 121 to 124 attached to the arms 111 to 114, respectively. When a surgical instrument moves in response to movement of an arm (any of the arms 111 to 114), a pivot position is a position in the surgical instrument at which the relative position between the surgical instrument and the arm to which the surgical instrument is attached is constant. The surgical instruments 121 to 124 are moved by the arms 111 to 114 with the pivot positions being fulcrums. The image 438 shows the distances between the respective pivot positions.

The image 439 shows settings of the operation device 2. The image 439 shows a load (weight of the hand controller 220) when the operator operates the operation part 221; a ratio (scaling) of an amount of movement of the hand controller 220 to an actual amount of movement of the surgical instrument; the height of the arm rest 203*a*; and the position (depth) of the foot unit 230 in the front-rear direction.

By referring to the images 438, 439, the observer can grasp the pivot positions of the surgical instruments 121 to 124 and the settings of the operation device 2.

The display selection area 431 may be provided with tabs other than the operation information tab and the setting information tab, and various information may be displayed in the information display area 430 in response to the other tabs being selected. For example, information on other equipment regarding the surgery may be displayed.

Figure 25:
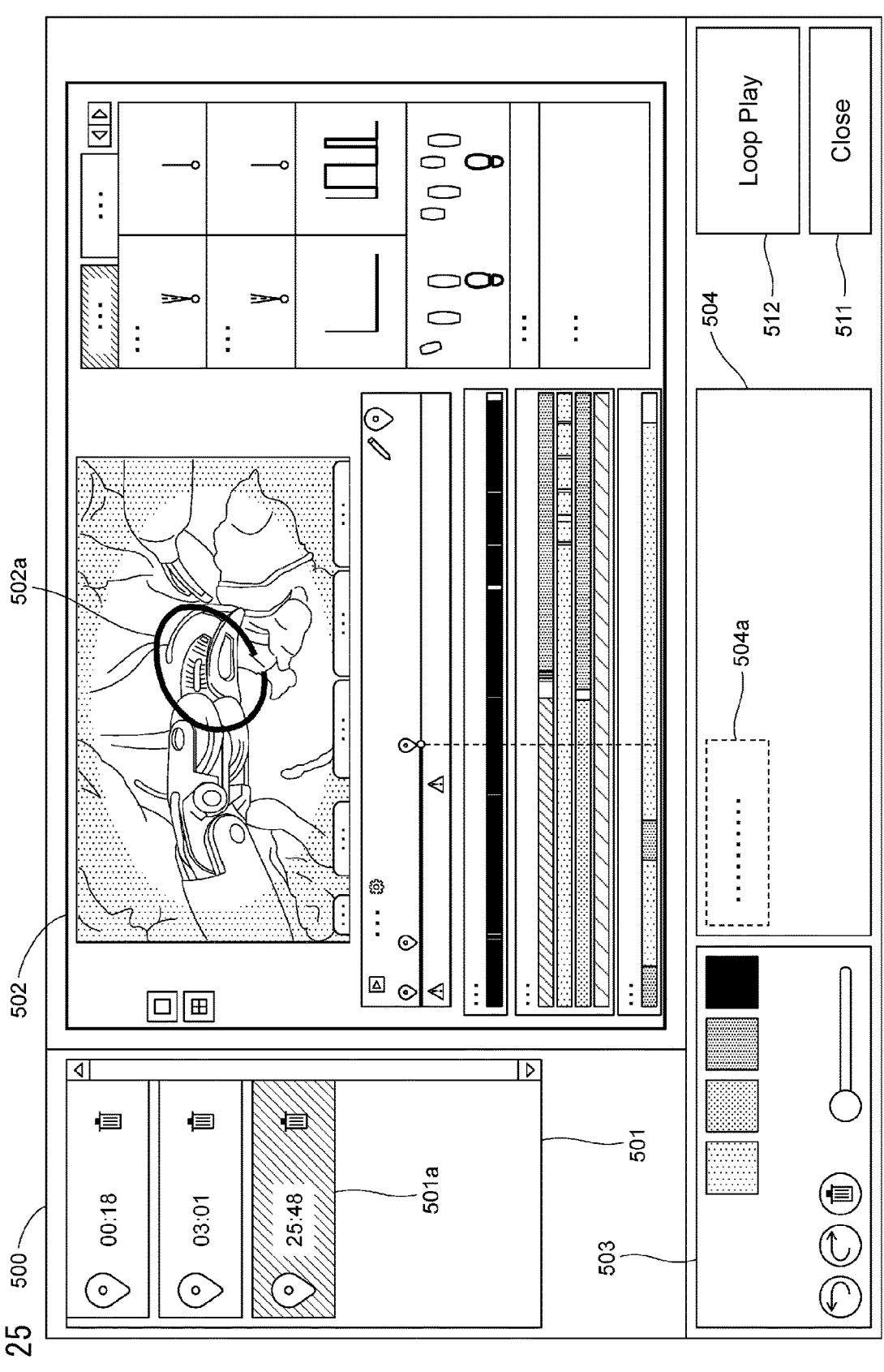
FIG. 25 schematically shows a configuration of an editing image displayed when a bookmark insertion button is operated in the surgical image, according to the embodiment.

FIG. 25 schematically shows the configuration of an editing image 500 displayed when the bookmark insertion button 425 is operated in the surgical image 400.

When the bookmark insertion button 425 is operated in the surgical image 400, the surgical image 400 at that time point is automatically stored as a screenshot 502 in the storage unit 322 of the information processing device 320.

The editing image 500 includes a bookmark display area 501, the screenshot 502, an editing tool area 503, a text input area 504, a close button 511, and a loop play button 512.

The bookmark display area 501 displays bookmark items 501*a* corresponding to set bookmarks. When a bookmark item 501*a* is operated, the bookmark item 501*a* is selected, and a screenshot 502, an image 502*a*, and a text 504*a* corresponding to the selected bookmark item 501*a* are displayed. When the bookmark insertion button 425 is operated in the surgical image 400 and the editing image 500 is displayed, the bookmark item 501*a* is in the selected state. When a trash box mark in the bookmark item 501*a* is operated, the corresponding bookmark is deleted.

The screenshot 502 is a screenshot of the surgical image 400 corresponding to the selected bookmark item 501*a*. The observer can insert a hand-drawn image 502*a* in the screenshot 502 by dragging the mouse over the screenshot 502. In addition, the observer can change the color, the line thickness, and the like of the figure to be drawn in the screenshot 502 by operating various buttons and a slider in the editing tool area 503. The observer can add the text 504*a* to the bookmark item 501*a* by selecting the text input area 504 and entering the text via the keyboard.

When the close button 511 is operated, the image 502*a* and the text 504*a* set in the editing image 500 are stored in association with the screenshot 502 into the storage unit 322 of the information processing device 320. Thereafter, the editing image 500 is closed and the surgical image 400 is again displayed. Since the screenshot 502, the image 502*a*, and the text 504*a* are stored, the observer can smoothly learn the operation performed by the operator by referring to the stored contents later.

When the loop play button 512 is operated, as in the case of the close button 511, the image 502*a* and the text 504*a* set in the editing image 500 are stored in association with the screenshot 502 into the storage unit 322 of the information processing device 320, and the editing image 500 is closed and the surgical image 400 is again displayed. In this case, in the surgical image 400, the moving image before and after (e.g., ±5 seconds) the bookmark corresponding to the bookmark item 501*a* selected when the editing image 500 was closed is repeatedly played. This allows the observer to smoothly proceed learning while repeatedly referring to the images in a scene that the observer desires to learn intensively.

The number of times the moving image is repeatedly played when the loop play button 512 is operated, is not particularly limited. The playback may be repeated until the observer makes an instruction to end the playback, or the playback may be ended when a predetermined number of times of repetitions has been reached. The moving image may not necessarily be repeatedly played, and may be ended after being played once.

If a lecture is performed with the observation terminal 340, a lecturer inserts a hand-drawn image 502*a* to draw the attention of students attending the lecture to an area indicated by the image 502*a*. This enables the students to smoothly learn the operation performed by the operator.

In FIG. 25, after the bookmark insertion button 425 has been operated in the surgical image 400, the hand-drawn image 502*a* is inserted in the screenshot 502. However, a hand-drawn image may be inserted in the surgical image 400 in advance.

Figure 26:
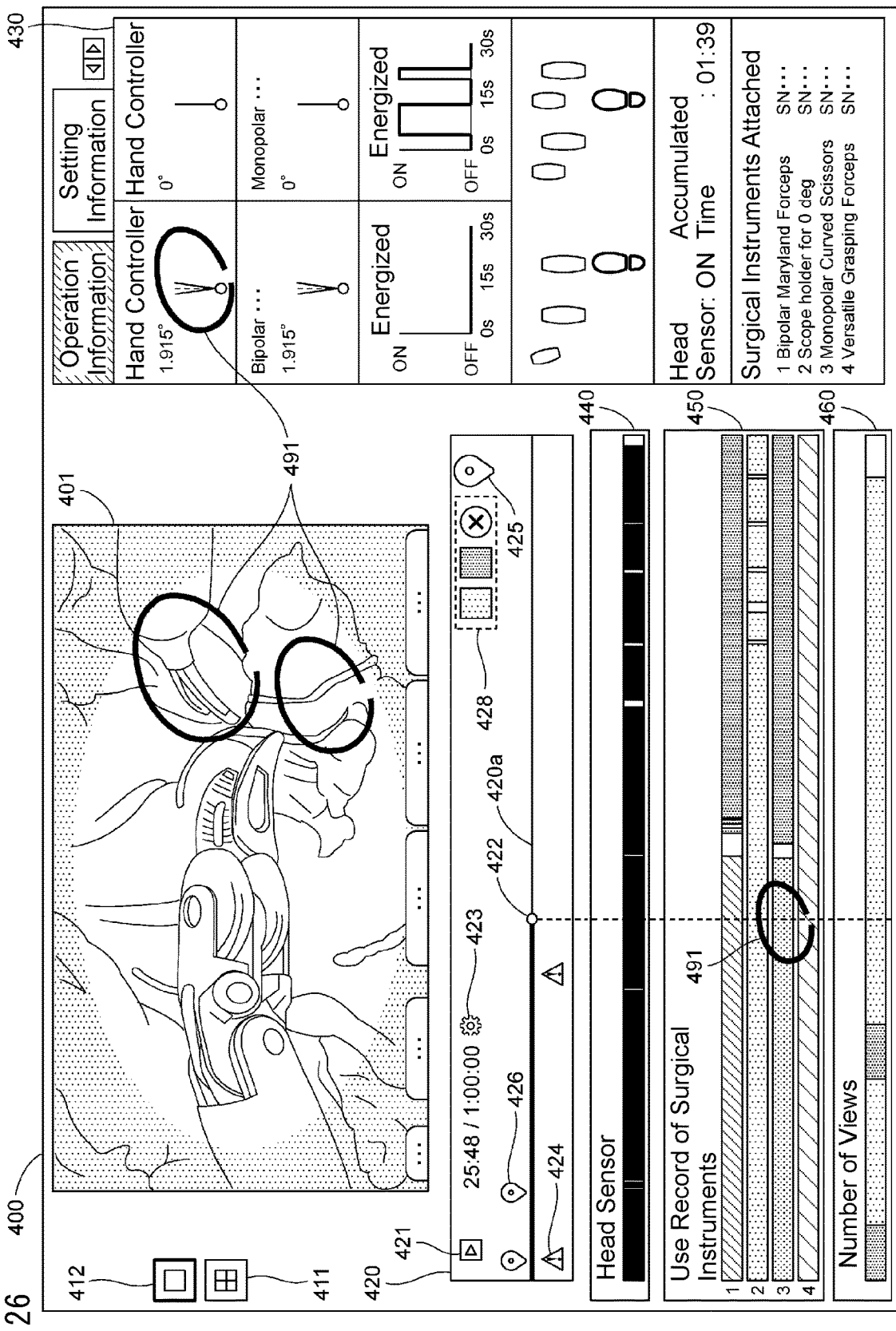
FIG. 26 schematically shows the configuration of the surgical image in which a hand-drawn image is inserted in advance, according to the embodiment.

FIG. 26 schematically shows the configuration of the surgical image 400 in the case where a hand-drawn image 491 is inserted therein in advance.

In the surgical image 400 shown in FIGS. 17, 18, when the editing start button 427 is operated, an editing tool area 428 is displayed instead of the editing start button 427 in the moving image control area 420 in the surgical image 400 as shown in FIG. 26. The editing tool area 428 includes an icon for changing the color of a hand-drawn line, and an end icon for ending the drawing.

In the surgical image 400 shown in FIG. 26, the observer inserts the hand-drawn image 491 by operating the mouse, and operates the bookmark insertion button 425. Thus, the screenshot 502 of the surgical image 400 and the hand-drawn image 491 are automatically stored in the storage unit 322 of the information processing device 320. Then, the editing image 500 including the screenshot 502 in which the hand-drawn image 491 is inserted, is displayed. Insertion of the hand-drawn image 491 may be performed while the surgical image 400 is being played, or may be performed with playback of the surgical image 400 being paused.

Next, processes performed by the control unit 321 of the information processing device 320 will be described with reference to FIGS. 27 to 30.

Figure 27:
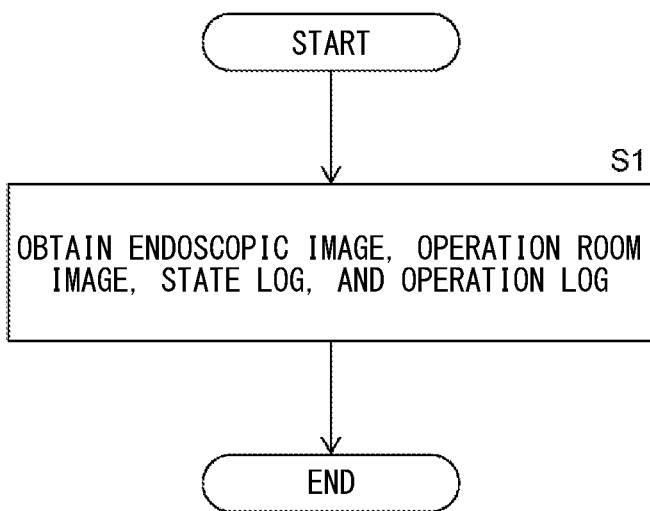
FIG. 27 is a flowchart showing a process of receiving information required for generation of the surgical image, according to the embodiment.

FIG. 27 is a flowchart showing a process of receiving information required for generation of the surgical image 400.

In step S1, the control unit 321 of the information processing device 320 receives the endoscopic image, the operation room image, the state log, and the operation log transmitted in real time from the storage device 310, and stores them in the storage unit 322. The state log includes: a log indicating the state (grip angle) of the operation part 221 based on the output of the encoder 261; a log indicating the states (movement amounts) of the movable parts 222 to 226 based on the outputs of the respective encoders 272 to 276; a log indicating the states (e.g., energized state or non-energized state) of the foot pedals 231 to 237 based on the outputs of the limit sensors 281 to 287; and a log indicating the state of the viewer 211 (whether or not the operator is close to the viewer) based on the output of the head sensor 212. The operation log includes a log indicating an operation (operation amount) of the operating unit 140 of the arm device 1 based on the output of the encoder 142.

Figure 28:
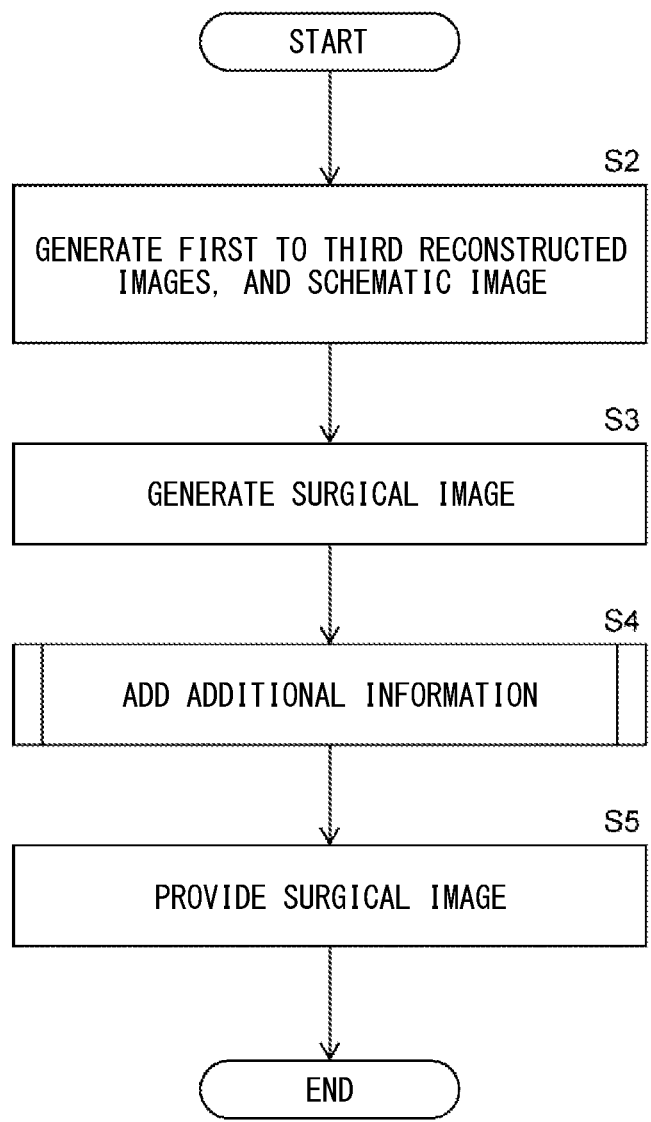
FIG. 28 is a flowchart showing a process of generating the surgical image, according to the embodiment.

FIG. 28 is a flowchart showing a process of generating the surgical image 400. The process shown in FIG. 28 is executed in response to a request from the observation terminal 340.

In step S2, the control unit 321 generates first to third reconstructed images on the basis of the state log and the operation log. The first reconstructed image includes images 432*a*, 432*b*, 434, 435, 440 visualizing operations to the operation targets (the operation part 221, the foot pedals 231 to 237, and the viewer 211) that the operator touches and operates. The second reconstructed image includes an image 435 schematically showing the operation preparing state with respect to the operation target (the foot pedals 231 to 237), i.e., the state in which the feet are positioned in front of or above the foot pedals. The third reconstructed image includes images 433a, 433b visualizing the motions of the forceps attached to the arm of the arm device 1.

In step S2, the control unit 321 generates the schematic image 404 on the basis of, out of the state log, the log indicating the state of the operation part 221 (grip angle; the 1_grip angle of the hand controller (right) and the 1_grip angle of the hand controller (left) in FIG. 13), and the log indicating the states of the movable parts 222 to 226 (movement amounts; the 1_1 shaft to 1_7 shaft of the hand controller (right) and the 1_1 shaft to 1_7 shaft of the hand controller (left) in FIG. 13), and generates the schematic image 403 on the basis of the operation log.

In step S3, the control unit 321 generates the surgical image 400 on the basis of the endoscopic image 401, the operation room image 402, the schematic images 403, 404 generated in step S2, and the first to third reconstructed images generated in step S2. In step S4, the control unit 321 adds additional information to the surgical image 400 generated in step S3.

Figure 29:
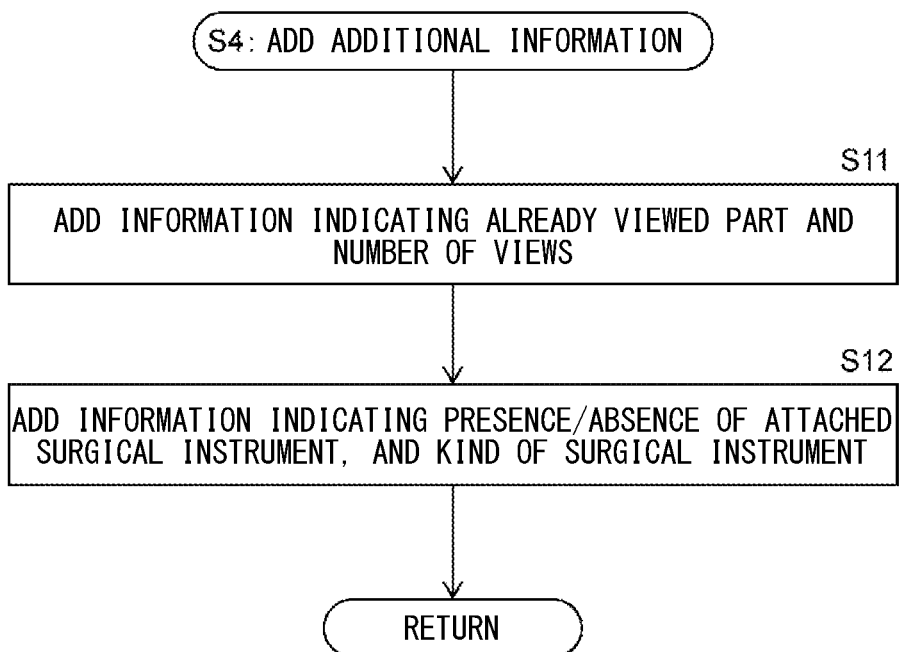
FIG. 29 is a flowchart showing in detail a process of adding additional information, according to the embodiment.

FIG. 29 is a flowchart showing in detail the process of adding the additional information in step S4 in FIG. 28.

In step S11, the control unit 321 of the information processing device 320 adds, to the surgical image 400, information indicating a part, of the endoscopic image 401 over the entire period, that has already been viewed, and the number of views (the image 460 showing the number of views, in FIG. 20). In step S12, the control unit 321 adds, to the surgical image 400, information indicating, in time series, whether or not the surgical instruments 121 to 124 are attached (the image 450 showing the use record of the surgical instruments, in FIG. 20), and information indicating the kinds of the surgical instruments (the surgical instrument information 451 in FIG. 20, and the image 437 in FIG. 21).

Referring back to FIG. 28, in step S5, the control unit 321 provides the observation terminal 340 with the surgical image 400 to which the additional information has been added in step S4. The control unit 321 executes the processes in steps S1 to S4 for the endoscopic image, the operation room image, the state log, and the operation log for a predetermined period, and thereafter, executes the process in step S5. The control unit 321 repeatedly executes the processes in steps S1 to S5 until receiving, from the observation terminal 340, an instruction to end display of the surgical image 400. Upon receiving the end instruction, the control unit 321 ends the process in FIG. 28.

The control unit 321 may execute the process in step S5 after executing the processes in steps S1 to S4 for the endoscopic image, the operation room image, the state log, and the operation log over the entire period. In this case, it is not necessary to repeat the processes in steps S1 to S5.

In the process shown in FIG. 28, in the process of providing the surgical image 400 in step S5, the control unit 321 provides the display unit 343 of the observation terminal 340 with an image (moving image) in which the endoscopic image 401, the operation room image 402, the schematic images 403, 404, the images in the moving image control area 420 and the information display area 430, and the images 440, 450, and 460 are synchronized with each other while changing over time.

Figure 30:
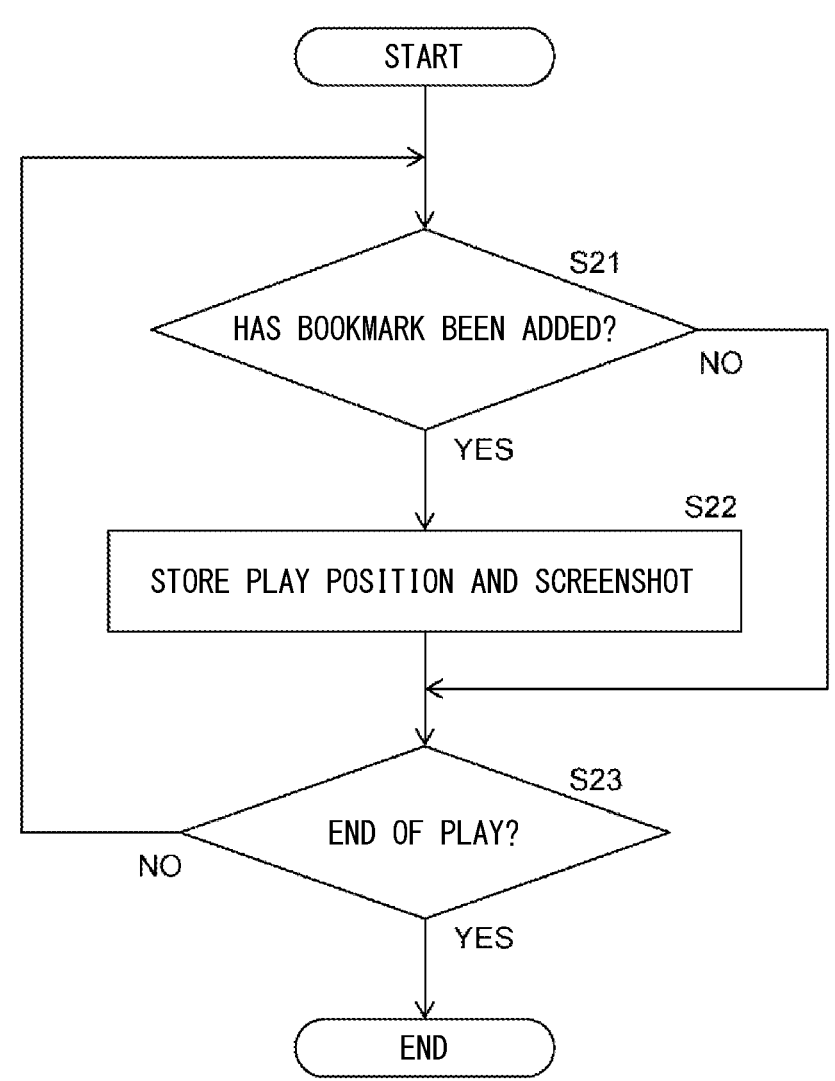
FIG. 30 is a flowchart showing a process regarding storage of a screenshot due to addition of a bookmark, according to the embodiment.

FIG. 30 is a flowchart showing a process regarding storage of the screenshot 502 due to addition of a bookmark.

In step S21, the control unit 321 of the information processing device 320 determines whether or not the bookmark insertion button 425 has been operated. If the bookmark insertion button 425 has been operated, the control unit 321, in step S22, stores the play position of the endoscopic image 401, and the screenshot of the surgical image 400 at the time when the bookmark insertion button 425 was operated. In step S23, the control unit 321 determines whether or not an instruction to end the playback of the surgical image 400 has been received from the observation terminal 340. If the end instruction has not been received, the control unit 321 returns the process to step S21. If the end instruction has been received, the control unit 321 ends the process in FIG. 30.

Figure 31:
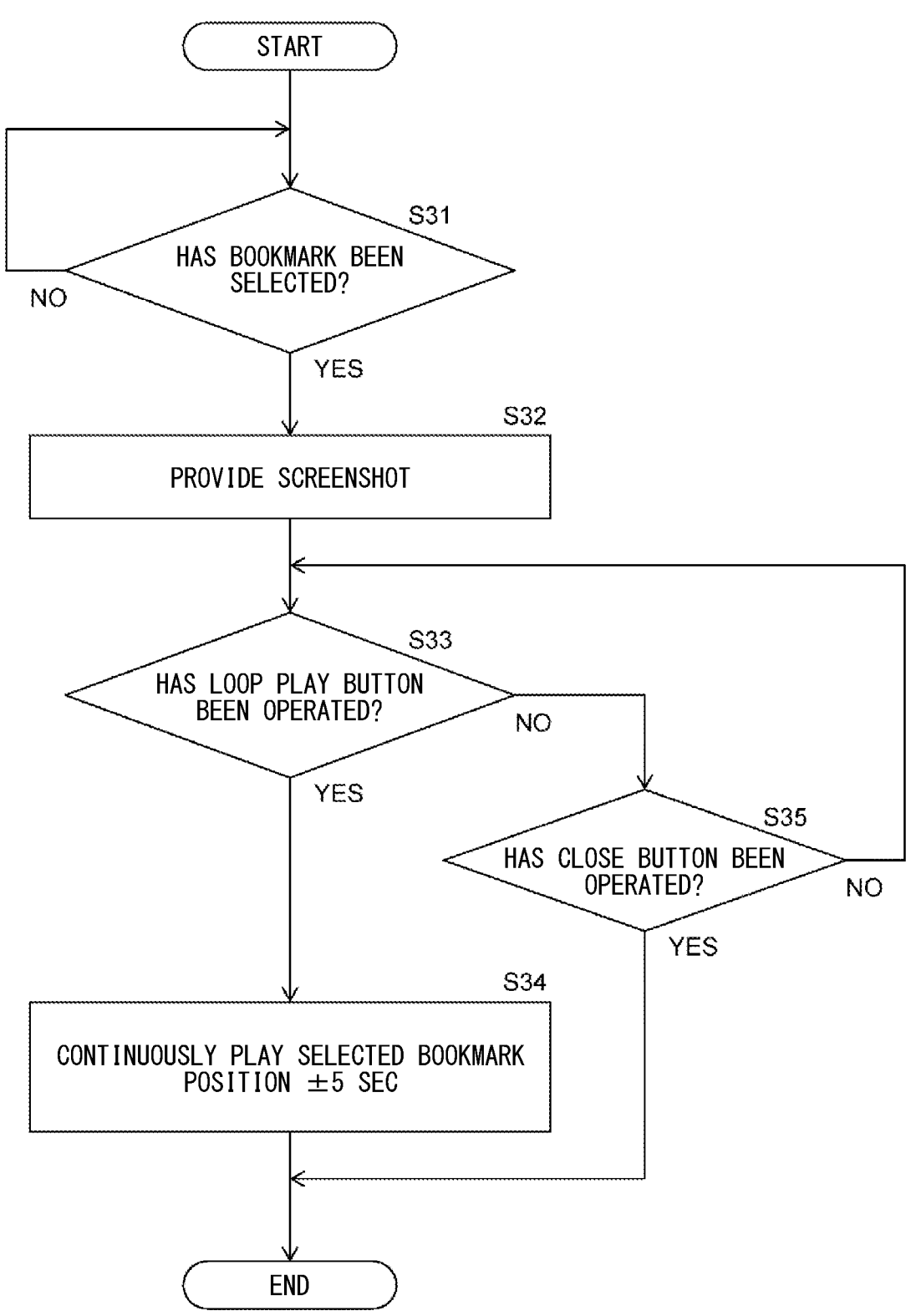
FIG. 31 is a flowchart showing a process regarding display of a screenshot and reproduction of the screenshot before and after a bookmark position.

FIG. 31 is a flowchart showing a process regarding display of the screenshot 502 and playback before and after the bookmark position.

In step S31, the control unit 321 of the information processing device 320 determines whether or not a bookmark has been selected. Selection of a bookmark is executed by the bookmark item 501a being operated in the editing image 500, the bookmark 426 being operated in the surgical image 400, or the bookmark insertion button 425 being operated in the surgical image 400.

If a bookmark has been selected, in step S32, the control unit 321 provides the observation terminal 340 with the corresponding screenshot 502, and the hand-drawn images 502a, 491 and the text 504a associated with the screenshot 502. Thus, as shown in FIG. 25, the editing image 500 including the screenshot 502, the images 502a, 491, and the text 504a is displayed on the display unit 343 of the observation terminal 340.

In step S33, the control unit 321 determines whether or not the loop play button 512 on the editing image 500 has been operated. When the loop play button 512 has been operated, the editing image 500 is closed and the surgical image 400 is displayed. Then, in step S34, the control unit 321 transmits the information to the observation terminal 340 so that a part corresponding to a predetermined period (e.g., from −5 seconds to +5 seconds) before and after the selected bookmark position is repeatedly played. That is, for example, a part corresponding to ±5 seconds with respect to the selected bookmark position is loop-played in the observation terminal 340. When the loop play button 512 has not been operated, the process proceeds to step S35.

In step S35, the control unit 321 determines whether or not the close button 511 in the editing image 500 has been operated. If the close button 511 has not been operated, the control unit 321 returns the process to step S33. If the close button 511 has been operated, the editing image 500 is closed, and the surgical image 400 is displayed. This is the end of the process in FIG. 31.

<Effects of Embodiment>

The control unit 321 of the information processing device 320 obtains the state log (see FIG. 13) indicating the state, of the operation target, that is changed when the operator operates the operation part 221 of the operation device 2 (see FIG. 4), the foot pedals 231 to 237 (see FIG. 5), and the viewer 211 (see FIG. 3) (operation target) (step S1 in FIG. 27), generates the images 432a, 432b, 434, 435 (see FIG. 21) visualizing the operation of the operator to the operation target, and the image 440 (see FIG. 20) (reconstructed image) on the basis of the state log (step S2), and provides the surgical image 400 (see FIGS. 17, 18) in which the endoscopic image 401 showing the motion of the surgical robot 4 or the surgical instruments 121 to 124 (see FIG. 2), the operation room image 402, and the schematic images 403, 404 (see FIG. 17) (motion image) are associated with the reconstructed image (step S5 in FIG. 28).

By referring to the motion image and the reconstructed image, the observer can easily and accurately confirm the motion of the surgical robot 4 or the surgical instruments 121 to 124, and the operation to the operation target for realizing the motion.

The operation part 221 (operation target) is moved according to the operation of the operator, and the state log includes information (position, amount of rotation, angle, presence/absence, etc.) based on the outputs of the encoder 261, the sensor, and the like (state detector) that detect the state of the operation part 221 (operation target). According to this configuration, the images 432a, 432b (reconstructed image) visualizing how the operator actually moves the operation target can be generated by using the outputs of the encoder 261 and the like that detect the state of the operation target of the operation device 2.

The operation part 221 (operation target) is moved according to the operation of the operator, and the reconstructed image includes the image 432a (see FIG. 21) (schematic image) schematically showing the degree of movement of the operation part 221 (operation target) due to the operation of the operator. According to this configuration, a delicate operation by the operator can be schematically visualized, so that the observer can intuitively grasp the degree of movement of the operation part 221 by the operator. Thus, for example, even an unskilled person can smoothly learn the operation skill of the skilled operator by confirming, in the image 432a, the delicate operation by the skilled operator.

The image 432a (schematic image) is an image obtained by schematizing the operation target on the plane where the pair of movable plates 221b of the operation part 221 (operation target) move. According to this configuration, by referring to the image 432a, the observer can accurately confirm the amount of movement on the plane where the pair of movable plates 221b move. Therefore, the observer can more accurately grasp the movement of the pair of movable plates 221b.

The reconstructed image includes the image 432b (see FIG. 21) showing, by a numerical value, the degree of movement of the operation part 221 (operation target) due to the operation of the operator. According to this configuration, the degree of movement of the operation target by the operator can be quantitatively indicated by a distance or an angle of the movement of the operation target, for example. Therefore, the observer can quantitatively grasp the degree of movement of the operation target. This allows the observer to efficiently and accurately learn the operation to the operation target, and easily imitate the technique of the expert.

The operation target includes the foot pedals 234 to 237 (manipulator) for switching between energization and non-energization of the forceps (electrical instrument) attached to the arm device 1. The state log includes information indicating switching between energization and non-energization by the foot pedals 234 to 237 (manipulator). The reconstructed image includes the image 434 (see FIG. 21) schematically showing the period during which the foot pedals 234 to 237 (manipulators) were operated. According to this configuration, when a surgical treatment is performed by the forceps (electrical instrument) to the affected part of the body shown in the endoscopic image 401, the observer using the observation terminal 340 can grasp whether the operator sporadically energizes the electrical instrument or continuously energizes the electrical instrument over a certain period. This allows the observer to learn how to perform energization of the electrical instrument such as an electro-cautery when dissecting or coagulating the affected part by using the electrical instrument.

The operation target includes the viewer 211 (display unit) for the operator to observe the endoscopic image 401. The state log includes information based on an output of the head sensor 212 (sensor) that detects the operator being close to the viewer 211. The reconstructed image includes the image 440 (see FIG. 20) schematically showing periods in which closeness of the operator to the viewer 211 is continued and periods in which the closeness is interrupted. The former periods indicate that the operator performs the surgical treatment while viewing the image on the viewer 211, and the latter periods indicate that the operator does not view the image on the viewer 211 and interrupts the surgical treatment. According to this configuration, the observer can grasp the interval of the surgical treatment by the operator, by referring to the image 440. This allows the observer to learn in what state, of the surgical treatment shown in the endoscopic image 401, he/she should interrupt the surgical treatment to make an instruction to the assistant, replace the forceps, or take a break, for example.

The reconstructed image includes the images 434, 435 each schematically showing the operation timings to the foot pedals 231 to 237 (operation target). The operation timings are indicated by the timing at which the signal value becomes ON in the image 434, and the timing at which a color is given to the periphery of any of the pedal images 471 to 477 (see FIG. 23) in the image 435. According to this configuration, the observer can easily grasp at what timing the operator operated the operation target in the surgical treatment shown in the endoscopic image 401.

Step S2 in FIG. 28 includes a process of generating the image 435 (second reconstructed image) schematically showing the operation preparing state, on the basis of the outputs of the foot sensors 241 to 248 (sensors) that detect the operation preparing state with respect to the foot pedals 231 to 237 (operation targets). In the surgical image 400, the motion image and the second reconstructed image are associated with each other. As shown in the lower stage of FIG. 22, when the foot images 481 are displayed and a color is not given to the peripheries of the pedal images corresponding to the foot images 481, it is found that the feet are in the operation preparing state with respect to the corresponding foot pedals. According to this process, the observer can easily grasp at what timing the operator performed preparation for the operation to the foot pedals 231 to 237 in the surgical treatment shown in the endoscopic image 401.

Step S1 in FIG. 27 includes a process of obtaining the operation log of the operating unit 140 of the arm device 1 that is driven by the operation to the operation part 221 (operation target). Step S2 in FIG. 28 includes a process of generating the images 433a, 433b (third reconstructed image) visualizing the drive state of the operating unit 140 on the basis of the operation log. In the surgical image 400, the endoscopic image 401, the operation room image 402, and the schematic images 403, 404 (motion image) are associated with the third reconstructed image. According to this process, the observer can compare the operation to the operation part 221 by the operator with how the operating unit 140 of the arm device 1 is actually driven according to the operation.

The operation device 2 includes the operation part 221 (operation target), and the movable parts 222 to 226 (second operation target) that move in conjunction with the operation part 221 (operation target) being touched and operated by the operator. The motion image includes the schematic image 404 completely visualizing movements of the operation part 221 and the movable parts 222 to 226 on the basis of the state log. According to this process, for example, by referring to the schematic image 404 together with the images 432a, 432b (reconstructed image), the observer can smoothly confirm how the hand controller 220 was actually moved according to the operation by the operator.

The control unit 321 of the information processing device 320 adds, to the surgical image 400, the image 460 regarding the number of views shown in FIG. 20, as information indicating a part, of the motion image over the entire period, that has already been viewed, and the number of views (step S11 in FIG. 29), and provides the surgical image 400 to which the image 460 is added (step S5 in FIG. 28). According to this process, the observer can grasp the surgical process having been frequently referred to so far, such as a process including difficult technique and operation. This allows the observer to efficiently learn the technique and the operation to the operation target.

The operation target that the operator touches and operates is the operation part 221 for opening and closing the tip of the forceps attached to the arm device 1. According to this configuration, the observer can grasp the manual operation of the expert to the operation target, and easily imitate the operation of the expert to the operation target.

The control unit 321 of the information processing device 320 adds, to the surgical image 400, the image 450 regarding the use record of the surgical instrument shown in FIG. 20, as information indicating, in time series, whether or not the surgical instruments 121 to 124 are attached, on the basis of the outputs of the sensors 151 to 154 that detect attachment/detachment of the surgical instruments 121 to 124 with respect to the arm device 1 (step S12 in FIG. 29), and provides the surgical image 400 to which the image 450 is added (step S5 in FIG. 28). According to this process, the observer can grasp timings of attachment/detachment and replacement of the surgical instruments 121 to 124 with respect to the arm device 1, in the surgical treatment shown in the endoscopic image 401. This allows the observer to easily imitate the technique of the expert using the surgical instruments 121 to 124.

The control unit 321 of the information processing device 320 adds, to the surgical image 400, the surgical instrument information 451 shown in FIG. 20 and the image 437 shown in FIG. 21, as information indicating the kinds of the surgical instruments 121 to 124 attached to the arm device 1 (step S12 in FIG. 29), and provides the surgical image 400 to which the surgical instrument information 451 and the image 437 are added (step S5 in FIG. 28). According to this process, the observer can grasp what kinds of surgical instruments are used according to the progress of the surgical treatment. This allows the observer to easily imitate the technique of the expert using the surgical instruments 121 to 124.

The operation target that the operator touches and operates is the foot pedals 231 to 237 of the operation device 2. According to this configuration, the observer can grasp the operation to the operation target by the expert's feet, and can easily imitate the operation by the expert's feet. For example, when the operation of the hand controller 220 is switched by the foot pedal 233 to adjustment of the angle of the endoscope 122, the observer can grasp how frequently the expert adjusts the angle of the endoscope 122, by referring to the image 435 (reconstructed image).

The foot pedals include the foot pedals 234 to 237 for the right foot, and the foot pedals 231 to 233 for the left foot. The observer can grasp the operations to the foot pedals 231 to 237 by the left foot and the right foot.

The operation target that the operator touches and operates includes the operation part 221 of the hand controller 220 and the foot pedals 231 to 237 for operating the surgical instruments 121 to 124 attached to the arm device 1. The reconstructed image includes the images 432a, 432b (first image) visualizing the operation to the operation part 221, and the images 434, 435 (second image) visualizing the operation to the foot pedals 231 to 237. In the surgical image 400, the images 432a, 432b (first image) are disposed above the image 435 (second image), as shown in FIG. 21. According to this configuration, the positions of the hands and feet of the operator in the up-down direction coincide with the positions of the operation targets in the up-down direction in the surgical image 400, so that the observer can more smoothly learn the operation by the operator.

In the process of providing the surgical image (step S5 in FIG. 28), the control unit 321 of the information processing device 320 changes the endoscopic image 401, the operation room image 402, the schematic images 403, 404 (motion image), and the images 432a, 432b, 434, 435 (reconstructed image) over time. According to this process, the motion image and the reconstructed image changing over time, i.e., the moving image, allow the observer to more smoothly grasp the operation to the operation target that follows the progress of the surgery.

In the process of providing the surgical image 400 (step S5 in FIG. 28), the control unit 321 of the information processing device 320 synchronizes the endoscopic image 401, the operation room image 402, and the schematic images 403, 404 (motion image) with the images 432a, 432b, 434, 435 (reconstructed image). According to this process, the observer can smoothly confirm the operation, to the operation target, corresponding to the surgical treatment shown in the motion image.

During display of the surgical image 400 that changes over time, the control unit 321 of the information processing device 320 receives designation of any time point via the bookmark insertion button 425 (step S21 in FIG. 30), and automatically stores the screenshot 502 (surgical image 400) at the designated time point (step S22). The observer can store the surgical image 400 at any time point, during display of the surgical image 400 that changes over time, and therefore can smoothly learn the operation for the surgical treatment.

For example, if the operation of the operator is so fast that the observer cannot smoothly compare the endoscopic image 401, the operation room image 402, and the schematic images 403, 404 (motion image) with the images 432a, 432b, 434, 435 (reconstructed image), the observer can store the screenshot 502 corresponding to the surgical image 400 at that time point, as shown in FIG. 25. In addition, if the observer takes a lecture of the expert after the surgery while referring to the surgical image 400 and the expert performs an insertion or the like to the surgical image 400 as shown in FIGS. 25, 26, the observer can store the images 502a, 491 corresponding to the insertion together with the screenshot 502 corresponding to the surgical image 400. Thus, the observer can smoothly learn the operation for the surgical treatment by referring to the stored screenshot 502 later.

During display of the surgical image 400 that changes over time, the control unit 321 of the information processing device 320 receives designation of any time point via the bookmark insertion button 425 (step S21 in FIG. 30), receives, via the loop play button 512, a play instruction at the designated time point (step S33 in FIG. 31), and plays the surgical image 400 for a predetermined period before and after the designated time point, on the basis of the play instruction (step S34). According to this process, by designating any time point during display of the surgical image 400 that changes over time, the observer can confirm, by playback, the motion image and the reconstructed image around the time point. For example, if the operation of the operator is so fast that the observer cannot smoothly compare the motion image with the reconstructed image, the observer, by designating the corresponding time point, can confirm, by playback, the motion image and the reconstructed image around the time point. This allows the observer to smoothly learn the operation for the surgical treatment.

Figure 32:
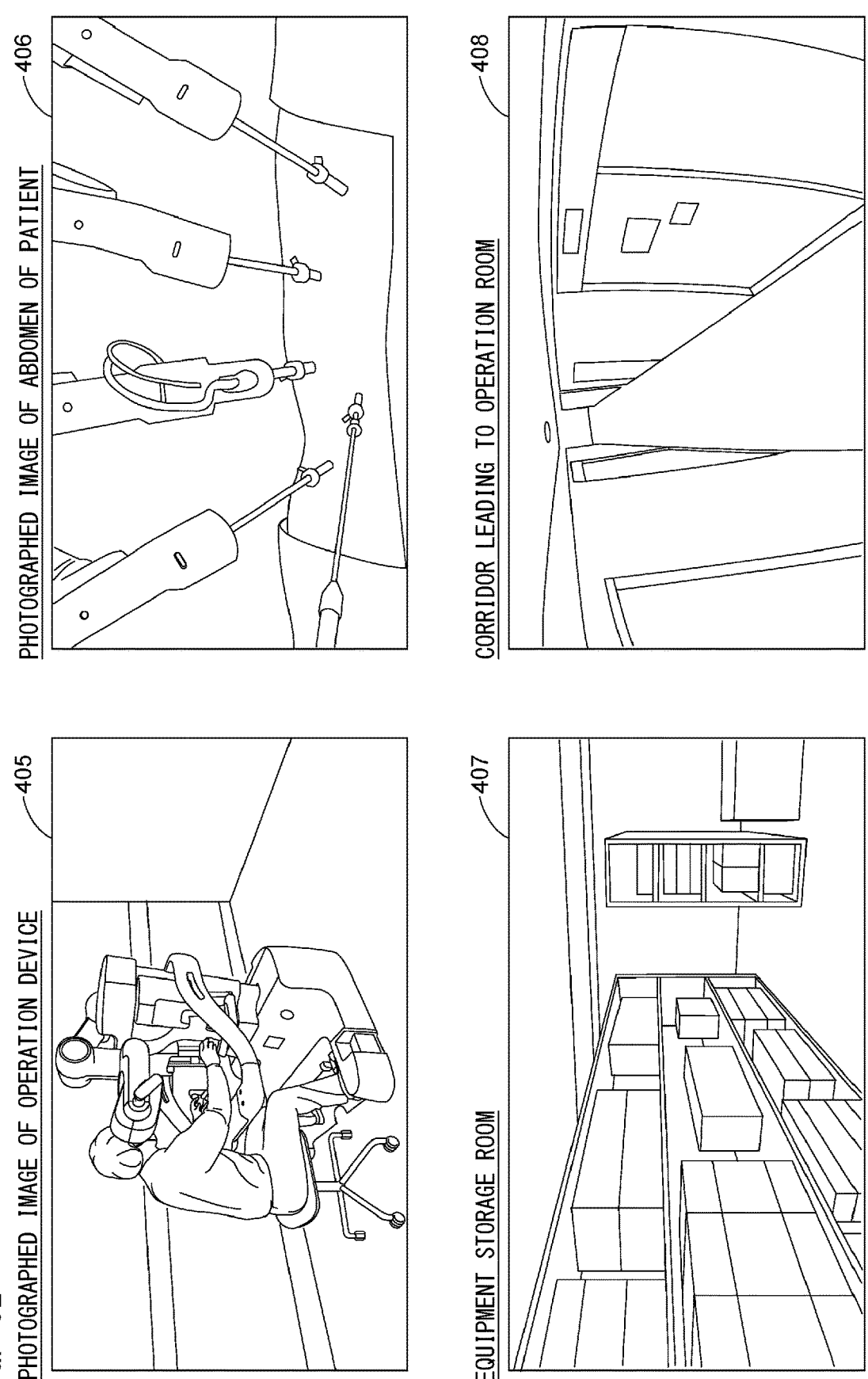
FIG. 32 schematically shows a captured image of the operation device, a captured image of the abdomen of a patient, a captured image of an equipment storage room, and a captured image of a corridor leading to an operation room, according to a modification of the embodiment.

As shown in FIG. 17, in the surgical image 400, the endoscopic image 401 and the schematic images 403, 404 (motion image) are associated with the operation room image 402 obtained from the operation room camera 301 that captures the image of the operation room where the arm device 1 is installed. As shown in FIG. 32, an image 405 of the operation device 2, an image 406 of the abdomen of the patient, an image 407 of an equipment storage room, an image 408 of a corridor leading to the operation room, and the like may be captured by cameras, and the images 405 to 408 may be displayed in the surgical image 400 together with the motion image. The images 405 to 408 in this case are moving images captured synchronously with the motion image.

As described above, in the surgical image 400, the endoscopic image 401 and the schematic images 403, 404 (motion image) are associated with an image obtained from a camera that captures at least one of: the operation room where the arm device 1 is installed; the operation device 2; the abdomen of the patient; the equipment storage room; and the corridor leading to the operation room, whereby the observer can confirm the states of the operation room, the operation device 2, the abdomen of the patient, the equipment storage room, and the corridor, according to the progress of the surgical treatment displayed in the motion image. For example, the observer can confirm the assistance provided by and the behavior of the assistant in the operation room, the angles of the joints of the hand controller 220 on the operation device 2, the angle of the trocar in the abdomen of the patient, and coming, going, and movement of the assistant in the equipment storage room and the corridor, according to the progress of the surgical treatment. This allows the observer to further learn how he/she and the team should behave during the surgical treatment.

The information processing system 5 shown in FIG. 8 includes the storage device 310 and the information processing device 320. The storage device 310 stores therein the state log indicating the state of the operation target that is changed when the operator operates the operation target of the operation device 2 for controlling the motion of the arm device 1 of the surgical robot 4 to which the surgical instruments 121 to 124 are attached. The operation target is, for example, the operation part 221 (see FIG. 4), the foot pedals 231 to 237 (see FIG. 5), and the viewer 211 (see FIG. 3). The information processing device 320 generates the images 432a, 432b, 434, 435, 440 (reconstructed image) visualizing the operation of the operator to the operation target, on the basis of the state log stored in the storage device 310, and provides the surgical image 400 in which the endoscopic image 401 indicating the motion of the surgical robot 4 or the surgical instruments 121 to 124, the operation room image 402, and the schematic images 403, 404 (motion image) are associated with the reconstructed image.

According to this configuration, the observer can easily and accurately confirm the motion of the surgical robot 4 or the surgical instruments 121 to 124 and the operation to the operation target for realizing the motion, by referring to the motion image and the reconstructed image.

<Modifications>

In the above embodiment, in the image 432a (see FIG. 21) showing the degree of movement of the operation part 221 due to the operation of the operator, the schematic diagram of the pair of movable plates 221b is displayed, and the degree of opening of the pair of movable plates 221b in the schematic diagram is rendered according to the operation of the operation part 221. However, the present disclosure is not limited thereto. Instead of the schematic diagram of the pair of movable plates 221b, a meter schematically showing the degree of opening of the pair of movable plates 221b may be displayed in the image 432a.

The image 432a is an image that two-dimensionally and schematically shows the pair of movable plates 221b (operation target) of the operation part 221, but may be an image that three-dimensionally and schematically shows the movable plate 221b (operation target).

In the above embodiment, in the image 434 shown in FIG. 21, the stepped-on states of the foot pedals corresponding to the left and right hand controllers 220 are indicated by ON or OFF. However, the present disclosure is not limited thereto. An output value indicating the intensity of energy that is applied to an electrocautery when the corresponding foot pedal is ON, may be displayed. In this case, the intensity of energy applied to the electrocautery when the foot pedal is ON may be changeable during the surgery according to setting of an energy generator. For example, if the intensity of energy applied to the electrocautery when the foot pedal is ON is set to V1, the height of the graph in the image 434 is V1 while the foot pedal is being stepped on. If the intensity of energy applied to the electrocautery when the foot pedal is ON is set to V2 (>V1), the height of the graph in the image 434 is V2 while the foot pedal is being stepped on. When the foot pedal is not stepped on, the height of the graph in the image 434 is 0.

In the above embodiment, in the image 434 shown in FIG. 21, the stepped-on states of the foot pedals 234 to 237 are displayed based on the state log. In addition, ON or OFF of a voltage actually applied to the forceps may be displayed based on the operation log.

In the above embodiment, the endoscopic image 401, the operation room image 402, and the schematic images 403, 404 are images that continuously change over time, i.e., moving images, and other parts of the surgical image 400 also continuously change over time. However, the present disclosure is not limited thereto. Each part of the surgical image 400 may be a plurality of static images (frame-by-frame moving image) that change at predetermined time intervals (e.g., several seconds). Even when repeated playback is performed by the loop play button 512 shown in FIG. 25, each part of the surgical image 400 may be a frame-by-frame moving image.

In the above embodiment, the endoscopic image 401, the operation room image 402, and the schematic images 403, 404 (motion image) are synchronized with the images 432a, 432b, 434, 435 (reconstructed image). However, the motion image and the reconstructed image may not necessarily be synchronized with each other as long as these images are associated with each other. For example, the reconstructed image may be displayed a little later than the motion image.

That is, the time at which the reconstructed image is displayed may be later than the time at which the motion image is displayed. The delay time of the reconstructed image may be adjusted so that the observer can easily learn the operation. In this case, after viewing the motion image, the observer moves his/her line of sight to the reconstructed image to confirm, in the reconstructed image, the operation that the observer has just viewed in the motion image.

Likewise, in the modification of the above embodiment, the images 405 to 408 (see FIG. 32) are synchronized with the motion image and the reconstructed image. However, the images 405 to 408 may not necessarily be synchronized with the motion image and/or the reconstructed image. The images 405 to 408 may not necessarily be moving images over the entire period of the motion image and/or the reconstructed image. The images 405 to 408 in a predetermined period may be displayed.

In the above embodiment, the screenshot 502 corresponding to the surgical image 400 is stored in the storage unit 322 of the information processing device 320 by the bookmark insertion button 425. However, the present disclosure is not limited thereto. The screenshot 502 may be stored in the storage unit 342 of the observation terminal 340.

In the above embodiment, the operation room image, the endoscopic image, the operation log, and the state log stored in the storage device 310 are transmitted to the information processing device 320 in real time during the surgery, but may be transmitted after the surgery.

In the above embodiment, the surgical image 400 includes the images 401 to 404, the images 432a to 435, and the like. However, the surgical image 400 may include at least one of the images 401 to 404 (motion image) and at least one of the images 432a, 432b, 434, 435, 440 (reconstructed image visualizing the operation of the operator). Even in this case, by referring to the motion image and the reconstructed image, the observer can easily and accurately confirm the motion of the surgical robot 4 or the surgical instruments 121 to 124 and the operation to the operation target for realizing the motion.

In the above embodiment, the state log and the operation log are composed of the current values obtained at predetermined time intervals. However, the present disclosure is not limited thereto. For example, each time the encoder or the sensor outputs a value or a signal, the control unit 131 or the control unit 251 may obtain the value or the signal as a current value, and at least one of the state log and the operation log may be composed of the current values.

In the above embodiment, the operation information tab and the setting information tab are displayed in the information display area 430 of the surgical image 400. Furthermore, an error information tab may also be displayed.

Figure 33:
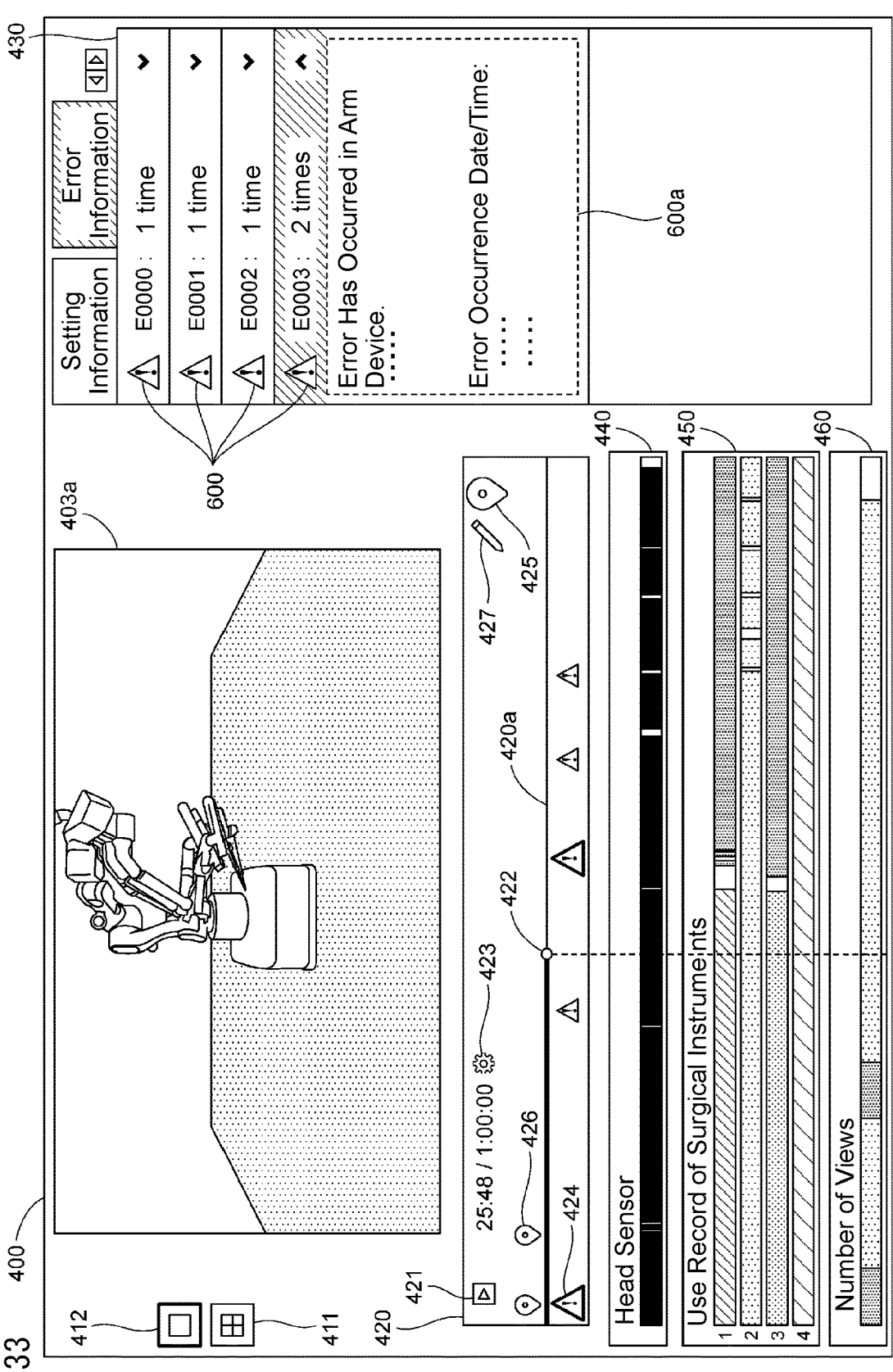
FIG. 33 schematically shows a configuration of a surgical image according to a modification of the embodiment.

FIG. 33 shows the surgical image 400 in the case where the error information tab is selected.

As shown in FIG. 33, when the error information tab is selected, pieces of error information 600 are displayed according to an error occurrence history. When one of the pieces of error information 600 is selected (in the example of FIG. 33, the fourth (lowermost) error information 600 is selected), detailed information 600a including an error message, occurrence date/time, and the like of the selected error is displayed. In addition, a warning mark 424 corresponding to the selected error information 600 is highlighted in the moving image control area 420. If the play position mark 422 is moved to the position of the warning mark 424, a static image 403a, of the device (arm device 1 in this example) having the error, at the time point when the error occurred, is displayed. The static image 403a is an image of the schematic image 403 (moving image) at the time point when the error occurred. This enables the observer to easily grasp when and what error occurred, and the operating state of the device having the error at the time point when the error occurred.

Moreover, in FIG. 33, after moving the play position mark 422 to the position of the warning mark 424, the observer may cause the same information as shown in FIG. 21 to be displayed in the information display area 430 by operating the operation information tab. Thus, the observer can refer to the reconstructed image visualizing the operation of the operator at the time point when the error occurred, while viewing the static image 403a at that time, and therefore, can grasp in detail the operation of the operator at the time point when the error occurred.

Various modifications of the embodiment of the present invention may be made as appropriate without departing from the scope of the technical idea defined by the claims.

What is claimed is:

1. A surgical robot system comprising a surgical robot, a storage device and an information processing device, wherein the surgical robot comprises:

a first arm to which a forceps is detachably attachable, the first arm having a motor operable to open and close the forceps;

a second arm to which an endoscope is detachably attachable, the endoscope being configured to capture a surgical motion image that shows operation of the forceps attached to the first arm;

an operation device including a hand controller comprising (i) a pair of movable members operable to change an angle between the pair of movable members to thereby open and close the forceps attached to the first arm, and (ii) a first detector configured to detect the angle between the pair of movable members; and an arm control device configured to monitor the angles between the pair of movable members detected by the first detector and operate the motor of the first arm to open and close the forceps based on the detected angle between the pair of movable members, the storage device is configured to communicate with the surgical robot and programmed to store a first set of log data representative of a change of the angle between the pair of movable members detected by the first detector during a first time interval and a series of the surgical motion images captured by the endoscope during a second time interval, wherein the first and second time intervals are at least partially co-temporal to each other; and the information processing device is configured to communicate with the storage device and programmed to:

obtain, from the storage device, the series of surgical motion images and the first set of log data, generate a first set of reconstructed motion images showing relative positions of the pair of movable members, based on the obtained the first set of log data; and play the first set of reconstructed motion images and the surgical motion image in synchronism with each other.

2. The system of claim 1, wherein the operation device further comprises a viewer screen configured to display the reconstructed motion images and the series of surgical motion images played by the information processing device.

3. The system of claim 1, wherein the reconstructed motion images include a schematic motion image showing the relative positions of the pair of movable members.

4. The system of claim 3, wherein the reconstructed motion images show, in a numerical form, the angle between the pair of the movable members.

5. The system of claim 1, wherein the first arm includes a second detector configured to detect a pinching angle indicative of a degree of pinching by the forceps, the storage device is configured to store a second set of log data representative of a change of the pinching angle detected by the second detector during the first time interval, and the information processing device is programmed to:
obtain, from the storage device, the second set of log data;
generate a second set of reconstructed motion images showing the degree of pinching by the forceps, based on the obtained second set of log data; and
play the first set of reconstructed motion images, the second set of reconstructed motion images and the surgical motion images in synchronism with each other.

6. The system of claim 5, wherein the second set of reconstructed motion images shows a schematic motion image showing the degree of pinching by the forceps.

7. The system of claim 6, wherein the second set of reconstructed motion images further shows, in a numerical form, the degree of pinching by the forceps.

8. The system of claim 1, wherein an electrocautery is detachably attached to the first arm, the operation device further includes a foot pedal and a third detector configured to detect a stepping operation of the foot pedal, wherein the electrocautery is energized by operation of the foot pedal, and the storage device is configured to store a third set of log data representative of a operation of the foot peal detected by the third detector during the first time interval, and the information processing device is programmed to:
obtain, from the storage device, the third set of log data;
generate a third set of reconstructed motion images showing a operation of the electrocautery, based on the obtained third set of log data; and
play the first set of reconstructed motion image, the third set of reconstructed motion images, and the surgical motion images in synchronism with each other.

9. The system of claim 8, wherein the information processing device is programmed to play the first set of reconstructed motion images and the third set of reconstructed motion images in such a manner that the first set of reconstructed motion images is displayed above the third set of reconstructed motion images on a viewer screen.

10. The system of claim 8, wherein the operation device further includes a fourth detector configured to detect a position of the foot of the operator on and near the foot pedal, the storage device is configured to store a fourth set of log data representative of the position of the foot of the operator detected by the fourth detector during the first time interval, and the information processing device is programmed to:
obtain, from the storage device, the fourth set of log data;
generate a fourth set of reconstructed motion images showing the position of the foot of the operator on and near the foot pedal based on the obtained fourth set of log data; and
play the first set of reconstructed motion images, the fourth set of reconstructed motion images, and the surgical motion images in such a manner that the first set of reconstructed motion images, the fourth set of reconstructed motion images, and the surgical motion images are shown in synchronism with each other.

11. The system of claim 1, wherein the operation device further includes a viewer screen configured to display the first set of reconstructed motion images and the surgical motion images and a fifth detector configured to detect a head position of the operator in front of the viewer screen, and the storage device is configured to store a fifth set of log data representative of a movement of the head position detected by the fifth detector during the first time interval, and the information processing device is programmed to:
obtain, from the storage device, the fifth set of log data; and
display a screen showing the movement of the head position based on the fifth set of log data on the viewer screen.

12. The system of claim 1, wherein the first arm includes a sixth detector configured to detect attachment and detachment of the forceps to and from the first arm, the storage device is configured to store a sixth set of log data representative of the attachment and detachment of the forceps detected by the sixth detector during the first time interval, and the information processing device is programmed to:
obtain, from the storage device, the sixth set of log data;
display a screen showing, based on the sixth set of log data, the attachment and detachment of the forceps to and from the first arm on a viewer screen operable to display the first set of reconstructed motion images and the surgical motion images.

13. The system of claim 12, wherein the arm control device is configured to determine a type of the forceps attached to the first arm, the storage device is configured to store a seventh set of log data representative of the type of forceps attached to the first arm during the first time interval, and the information processing device is programmed to:
obtain, from the storage device, the seventh set of log data; and
display on the viewer screen the type of forceps attached to the first arm based on the seventh set of log data.

* * * * *